US006555107B2

(12) United States Patent
Poeschla et al.

(10) Patent No.: US 6,555,107 B2
(45) Date of Patent: Apr. 29, 2003

(54) LENTIVIRAL NUCLEIC ACIDS AND USES THEREOF

(75) Inventors: Eric M. Poeschla, San Diego, CA (US); David J. Looney, Encinitas, CA (US); Flossie Wong-Staal, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/837,644

(22) Filed: Apr. 17, 2001

(65) Prior Publication Data

US 2001/0016347 A1 Aug. 23, 2001

Related U.S. Application Data

(63) Continuation of application No. 08/936,633, filed on Sep. 24, 1997, now abandoned.

(51) Int. Cl.[7] ...................... A61K 48/00; C12N 15/867; C12N 15/63; C12N 5/10; C07H 21/04
(52) U.S. Cl. ................... 424/93.2; 435/320.1; 435/325; 435/366; 435/235.1; 435/455; 435/456; 435/457; 536/23.1; 536/23.72; 536/24.1; 536/24.5; 424/93.1; 424/93.2; 424/93.6
(58) Field of Search .............................. 435/320.1, 325, 435/366, 235.1, 455, 456, 457; 536/23.1, 23.72, 24.1, 24.5; 424/93.1, 93.2, 93.6

(56) References Cited

U.S. PATENT DOCUMENTS

| | | |
|---|---|---|
| 4,683,202 A | 7/1987 | Mullis |
| 5,254,678 A | 10/1993 | Haseloff et al. |
| 5,279,833 A | 1/1994 | Rose |
| 5,426,039 A | 6/1995 | Wallace et al. |
| 5,641,662 A | 6/1997 | Debs et al. |
| 5,650,309 A | 7/1997 | Wong-Staal et al. |
| 5,681,746 A | 10/1997 | Chiron |
| 5,994,136 A | 11/1999 | Naldini et al. |
| 6,004,799 A | * 12/1999 | Luciw et al. ............... 435/236 |
| 6,013,516 A | 1/2000 | Verma et al. |
| 6,165,782 A | 12/2000 | Naldini et al. |

FOREIGN PATENT DOCUMENTS

| | | |
|---|---|---|
| EP | 0 360 257 | 3/1990 |
| WO | WO 91/06309 | 5/1991 |
| WO | WO 92/21750 | 12/1992 |
| WO | WO 93/24640 | 12/1993 |
| WO | WO 94/24298 | 10/1994 |
| WO | WO 94/268777 | 10/1994 |
| WO | WO 95/25547 | 9/1995 |
| WO | WO 95/25806 | 9/1995 |
| WO | WO 95/30755 | 11/1995 |
| WO | WO 95/32300 | 11/1995 |
| WO | WO 96/14332 | 5/1996 |
| WO | WO 96/21035 | 7/1996 |
| WO | WO 96/28563 | 9/1996 |
| WO | WO 96/37623 | 11/1996 |
| WO | WO 97/08330 | 3/1997 |
| WO | WO 97/32983 | 9/1997 |
| WO | WO 97/42338 | 11/1997 |
| WO | WO 97/48277 | 12/1997 |
| WO | WO 98/17816 | 4/1998 |
| WO | WO 99/36511 | 7/1999 |

OTHER PUBLICATIONS

Emerman, Nature Biotechnology (1996) 14:943.
Mitrophanous et al., Gene Therapy (1999) 6:1808–1818.
Naldini et al., Science (1996) 272:263–267.
Addison et al., Proc. Natl. Acad. Sci. USA (1995) 92:8522–8526.
Aldovini and Young, Journal of Virology (1990) 64(5):1920–1926.
Bandecchi et al., New Microbiologica (1995) 18:241–252.
Barr et al., J. Virol. (1995) 69:7371–7374.
Barr, Virology (1997) 228:84–91.
Bendinelli et al., Clinical Microbiology Reviews (1995) 8:87–112.
Bennet and Smyth, British Veterinary Journal (1992) 148:399–412.
Berson et al., Journal of Virology (1996) 70:6288–6295.
Blomer et al., J. Virol. (1997) 71(9):6641–6649.
Brown et al., Journal of Zoo and Wildlife Medicine (1993) 24:357–364.
Carey and Dalziel, British Veterinary Journal (1993) 149:437–454.
Carpenter and O'Brien, Current Opinion in Genetics and Development (1995) 5:739–745.
Chatterjee et al., Science (1992) 258:1485–1488.
Chen et al., Proc. Natl. Acad. Sci. USA (1994) 91:3054–3057.
Clapham et al., Journal of Virology (1992) 66:3531–3537.
Clayman et al., Cancer Res. (1995) 5:1–6.
Clements and Zink, Clinical Microbiology Reviews (1996) 9:100–117.
Clever et al., Journal of Virology (1995) 69(4):2101–2109.
Colak et al., Brain Res. (1995) 691:76–82.
Cornetta et al., Hum. Gene Ther. (1991) 2:215.

(List continued on next page.)

*Primary Examiner*—David Guzo
(74) *Attorney, Agent, or Firm*—Morrison & Foerster LLP

(57) ABSTRACT

The invention provides non-primate lentiviral vectors, packaging cells and packaging plasmids based, for example, on feline and ungulate retroviruses. In particular, the packaging plasmids are designed for expression in human cells (which are also used as packaging cells). The vectors of the invention transduce human cells, including difficult to target non-dividing cells of the hematopoietic and nervous system, in vitro and in vivo. The vectors are suitable for general gene transfer to these cells and for gene therapy to treat conditions mediated by these non-dividing cells including cancer and HIV infection.

46 Claims, 3 Drawing Sheets

OTHER PUBLICATIONS

Courchamp and Pontier, Feline Immunodeficiency Virus: An Epidemiological Review, Comptes Rendus de L'Academie des Sciences, Serie III, Sciences de la Vie (1994) 317:1123–1134.
Crystal, Science (1995) 270:404–410.
Elder and Phillips, Infectious Agents and Disease (1993) 2:361–374.
Elder et al., Advances in Virus Research (1995) 45:225–247.
Elshami et al., Human Gene Ther. (1996) 7:141–148.
Endres et al., Cell (1996) 87:745–756.
Felgner et al., Proc. Natl. Acad. Sci. USA (1987) 84:7413–7414.
Gardner and Luciw, Faseb Journal (1989) 3:2593–2606.
Gilden et al., Archives of Virology (1981) 67:181–185.
Haase, Annals of the New York Academy of Sciences (1994) 724:75–86.
Haddada et al., Curr. Top. Microbiol. Immunol. (1995) 199(Pt. 3):297–306.
Harouse et al., Journal of Virology (1995) 69:7383–7390.
Harouse and Gonzalez–Scarano, Journal of Virology (1996) 70:7290–7294.
Higgins and Sharp, Cabios (1989) 5:151–153.
Hwang et al., An. J. Respir. Cell Mol. Biol. (1995) 13:7–16.
Kolberg, J. NIH Res. (1992) 4:43.
Leavitt et al., Human Gene Therapy (1994) 5:1115–1120.
Mannino and Gould–Fogerite, BioTechniques (1988) 6(7):682–691.
McAllister et al., Nature New Biol. (1972) 235:3–6.
McKnight et al., Virology (1994) 201:8–18.
Meyers and Miller, Computer Applic. Biol. Sci. (1988) 4:11–17.
Miller et al., Mol. Cell. Biol. (1990) 10:4239.
Miyazawa et al., Archives of Virology (1994) 134:221–234.
Miyazawa et al., Journal of General Virology (1992) 73:1543–1546.
Morgan et al., Nucleic Acids Res. (1992) 20(6):1293–1299.
Naldini et al. Proc. Natl. Acad. Sci. (1996) 93:11382–11388.
Needleman and Wunsch, J. Mol. Biol. (1970) 48:443.
Olmsted et al., J. Virol. (1992) 66:6008–6018.
Olmsted et al., PNAS USA (1989) 86:2448–2452.
Olmsted et al., PNAS USA (1989) 86:8088–8092.
O'Malley et al., Cancer Res. (1995) 55:1080–1085.
Parolin et al., Virology (1996) 222:415–422.
Paulus et al., J. Virol. (1996) 70(1):62–67.
Pearson and Lipman, Proc. Natl. Acad. Sci. USA (1988) 85:2444.
Pedersen et al., Science (1987) 235:790–793.
Pedersen, The Feline Immunodeficiency Virus, in The Retroviridae, Levy (ed.) pp. 181–228, Plenum Press, New York (1993).
Poeschla et al., J. Virol. (1998) 72(8):6858–6866.
Poeschla et al., Nature Medicine (1998) 4(3):354–357.
Potempa et al., Journal of Virology (1997) 71:4419–4424.
Poznansky et al., Journal of Virology (1991) 65(1):532–536.
Reeves et al., Virology (1997) 231:130–134.
Rosenburg and Fauci, in Fundamental Immunology, Third Edition, Paul (ed.) Raven Press, Ltd. New York (1993).
Saveria–Campo, in DNA Cloning vol. II a Proactical Appraoch, Glover (ed.) IRL Press, Arlington, Virginia (1985) pp. 213–238.
Shelton et al., Journal of Acquired Immune Deficiency Syndromes (1990) 3:623–630.
Simon et al., Journal of Virology (1995) 69:4166–4172.
Smith and Waterman, Adv. Appl. Math. (1981) 2:482.
Sparger, Veterinary Clinics of North America, Small Animal Practice (1993) 23:173–191.
Sparger et al., Virology (1992) 187:165–177.
Sparger et al., Virology (1994) 205:546–553.
Srinivasakumar et al., J. Virol. (1997) 71(8):5841–5848.
Stoye and Coffin, Nature Medicine (1995) 1:1100.
Takeuchi et al., Journal of Virology (1994) 68:8001–8007.
Talbot et al., Journal of Virology (1995) 69:3399–3406.
Talbott, Proc. Natl. Acad. Sci. USA (1989) 86:5743–5747.
Tateno et al., Proc. Natl. Acad. Sci. USA (1989) 86:4287–4290.
Thormar and Sigurdardottir, Acta Pathol. Microbiol. Scandinav. (1962) 55:180–186.
Tomonaga et al., Journal of Veterinary Medical Science (1994) 56:199–201.
Tong et al., Gynecol. Oncol. (1996) 61:175–179.
Van Der Kuyl et al., Journal of Virology (1997) 71:3666–3676.
Vincent et al., J. Neurosurg. (1996) 85:648–654.
Wagaman et al., Virology (1993) 196:451–457.
Waters et al., Virology (1996) 215:10–16.
Willet, Immunology (1994) 81:228–233.
Willet, Journal of General Virology (1997) 78:611–618.
Yamada et al., Gene Therapy (1994) 1:38–45.
Yu et al., Gene Therapy (1994) 1:13–26.
Yu et al., PNAS (1995) 92:699–703.

* cited by examiner

SEQUENCE LISTING

<160> NUMBER OF SEQ ID NOS: 11

<210> SEQ ID NO 1
<211> LENGTH: 47

```
<212> TYPE: DNA
<213> ORGANISM: Artificial Sequence
<220> FEATURE:
<223> OTHER INFORMATION: Synthetic construct FIV 34TF10

<400> SEQUENCE: 1
cattgtaaga gtatataacc agtgctttgt gaaacttcga ggagtct                47

<210> SEQ ID NO 2
<211> LENGTH: 46
<212> TYPE: DNA
<213> ORGANISM: Artificial Sequence
<220> FEATURE:
<223> OTHER INFORMATION: Synthetic construct

<400> SEQUENCE: 2
ggtgggaggt ctatataagc agagctctct ggctaactag agaacc                 46

<210> SEQ ID NO 3
<211> LENGTH: 47
<212> TYPE: DNA
<213> ORGANISM: Artificial Sequence
<220> FEATURE:
<223> OTHER INFORMATION: Synthetic construct CT5

<400> SEQUENCE: 3
ggtgggaggt ctatataagc agagctctgt gaaacttcga ggagtct                47

<210> SEQ ID NO 4
<211> LENGTH: 32
<212> TYPE: DNA
<213> ORGANISM: Artificial Sequence
<220> FEATURE:
<223> OTHER INFORMATION: Synthetic construct

<400> SEQUENCE: 4
atatagagct ctgtgaaact cgaggagtc tc                                 32

<210> SEQ ID NO 5
<211> LENGTH: 25
<212> TYPE: DNA
<213> ORGANISM: Artificial Sequence
<220> FEATURE:
<223> OTHER INFORMATION: Antisense PCR primer

<400> SEQUENCE: 5
ccaatctcgc ccctgtccat tcccc                                        25

<210> SEQ ID NO 6
<211> LENGTH: 313
<212> TYPE: DNA
<213> ORGANISM: Artificial Sequence
<220> FEATURE:
<223> OTHER INFORMATION: 310 bp resulting fragment

<400> SEQUENCE: 6
gagctctgtg aaacttcgag gagtctcttt gttgaggact tttgagttct cccttgaggc   60
tcccacagat acaataaata tttgagattg aaccctgtcg agtatctgtg taatcttttt  120
tacctgtgag gtctcggaat ccgggccgag aacttcgcag ttggcgcccg aacagggact  180
tgattgagag tgattgagga agtgaagcta gagcaataga aagctgttaa gcagaactcc  240
tgctgaccta aatagggaag cagtagcaga cgctgctaac agtgagtatc tctagtgaag  300
cggactcgag ctc                                                    313
```

```
<210> SEQ ID NO 7
<211> LENGTH: 74
<212> TYPE: DNA
<213> ORGANISM: Artificial Sequence
<220> FEATURE:
<223> OTHER INFORMATION: Synthetic construct

<400> SEQUENCE: 7
acgtataagt tgttccattg taagagtata taaccagtgc tttgtgaaac ttcgaggagt      60
ctctttgttg agga                                                      74

<210> SEQ ID NO 8
<211> LENGTH: 56
<212> TYPE: DNA
<213> ORGANISM: Artificial Sequence
<220> FEATURE:
<223> OTHER INFORMATION: Synthetic  construct

<400> SEQUENCE: 8
aggcgtgtac ggtgggaggt ctatataagc agagctctct ggctaactag agaacc         56

<210> SEQ ID NO 9
<211> LENGTH: 69
<212> TYPE: DNA
<213> ORGANISM: Artificial Sequence
<220> FEATURE:
<223> OTHER INFORMATION: Synthetic construct

<400> SEQUENCE: 9
aggcgtgtac ggtgggaggt ctatataagc agagctctgt gaaacttcga ggagtctctt     60
tgttgagga                                                             69

<210> SEQ ID NO 10
<211> LENGTH: 30
<212> TYPE: DNA
<213> ORGANISM: Artificial Sequence
<220> FEATURE:
<223> OTHER INFORMATION: Primer F3'S

<400> SEQUENCE: 10
tatatagtcg actagggact gtttacgaac                                      30

<210> SEQ ID NO 11
<211> LENGTH: 34
<212> TYPE: DNA
<213> ORGANISM: Artificial Sequence
<220> FEATURE:
<223> OTHER INFORMATION: Primer F3'A/Not

<400> SEQUENCE: 11
atatatagtc gacgcggccg ctgcgaagtt ctcg                                 34
```

LENTIVIRAL NUCLEIC ACIDS AND USES THEREOF

This application is a Continuation of Ser. No. 08/936,633, filed Sep. 24, 1997, now abandoned.

STATEMENT OF GOVERNMENT SUPPORT

This invention was made with government support awarded by the Veteran's Administration and under Grant No. Ca 67394 and AI36612 awarded by the National Institutes of Health. The Government has certain rights in this invention.

BACKGROUND OF THE INVENTION

Gene therapy provides methods for combating chronic infectious diseases (e.g., HIV infection), as well as non-infectious diseases including cancer and some forms of congenital defects such as enzyme deficiencies. Several approaches for introducing nucleic acids into cells in vivo, ex vivo and in vitro have been used. These include liposome based gene delivery (Debs and Zhu (1993) WO 93/24640 and U.S. Pat. No. 5,641,662); Mannino and Gould-Fogerite (1988) *BioTechniques* 6(7): 682–691; Rose U.S. Pat No. 5,279,833; Brigham (1991) WO 91/06309; and Felgner et al. (1987) *Proc. Natl. Acad. Sci. USA* 84: 7413–7414) and adenoviral vector mediated gene delivery, e.g., to treat cancer (see, e.g., Chen et al. (1994) *Proc. Nat'l. Acad. Sci. USA* 91: 3054–3057; Tong et al. (1996) *Gynecol. Oncol.* 61: 175–179; Clayman et al. (1995) *Cancer Res.* 5: 1–6; O'Malley et al. (1995) *Cancer Res.* 55: 1080–1085; Hwang et al. (1995) *Am. J. Respir. Cell Mol. Biol.* 13: 7–16; Haddada et al. (1995) *Curr. Top. Microbiol. Immunol.* 199 (Pt. 3): 297–306; Addison et al. (1995) *Proc. Nat'l. Acad. Sci. USA* 92: 8522–8526; Colak et al. (1995) *Brain Res.* 691: 76–82; Crystal (1995) *Science* 270: 404–410; Elshami et al. (1996) *Human Gene Ther.* 7: 141–148; Vincent et al. (1996) *J. Neurosurg.* 85: 648–654). Replication-defective retroviral vectors harboring a therapeutic polynucleotide sequence as part of the retroviral genome have also been used, particularly with regard to simple MuLV vectors. See, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)).

One of the most attractive targets for gene therapy is HIV infection. The pandemic spread of HIV has driven an intense world-wide effort to unravel the molecular mechanisms and life cycle of these viruses. It is now clear that the life cycle of HIVs provide many potential targets for inhibition by gene therapy, including cellular expression of transdominant mutant gag and env nucleic acids to interfere with virus entry, TAR (the binding site for tat, which is typically required for transactivation) decoys to inhibit transcription and trans activation, and RRE (the binding site for Rev; i.e., the Rev Response Element) decoys and transdominant Rev mutants to inhibit RNA processing. See, Rosenburg and Fauci (1993) in *Fundamental Immunology, Third Edition* Paul (ed) Raven Press, Ltd., New York and the references therein for an overview of HIV infection and the HIV life cycle. Gene therapy vectors encoding ribozymes, antisense molecules, decoy genes, transdominant genes and suicide genes, including retroviruses are described in Yu et al., *Gene Therapy* (1994) 1:13–26. Antisense and ribozyme therapeutic agents are of increasing importance in the treatment and prevention of HIV infection.

Despite the various gene therapeutic approaches now underway for treating cancer, HIV and the like, there are a variety of limitations of the delivery systems currently used in gene therapy. For instance, with regard to HIV treatment, the extensively used murine retroviral vectors transduce (transfer nucleic acids into) human peripheral blood lymphocytes poorly, and fail to transduce non-dividing cells such as monocytes/macrophages, which are known to be reservoirs for HIV. New safer vectors for the delivery of viral inhibitors, particularly to non-dividing hematopoietic stem cells for the treatment of HIV infection, are desirable.

Non-primate lentiviruses provide a possible system for the development of new vector systems; however, relatively little is known about these viruses. Although their biology has received considerably less scrutiny than that of the primate lentiviruses (e.g., HIV-1, HIV-2 and SIV), non-primate lentiviruses are of interest for comparative lentivirus biology and as potential sources of safer lentiviral vectors. HIV-based retroviral vectors have recently shown promise for therapeutic gene transfer because they display the lentiretrovirus-specific property of permanently infecting non-dividing cells (see, Naldini et al. (1996) *Science* 272, 263–267). In contrast, retroviral vectors derived from simpler retroviruses (e.g., the Oncovirinae) require breakdown of the nuclear envelope during mitosis to complete reverse transcription and integration. Consequently, these vectors transduce non-dividing cells poorly, which may limit usefulness for gene transfer to quiescent or post-mitotic cellular targets. However, HIV vectors present complex safety problems (see, Emerman (1996) *Nature Biotechnology* 14, 943).

The non-primate lentiviruses include the ungulate lentiviruses, including visna/maedi virus, caprine arthritis encephalitis virus (CAEV), equine infectious anemia virus (EIAV), and bovine immunodeficiency virus (BIV). These lentiviruses only infect hoofed animals (ungulates) and generally only infect particular species of ungulates.

The non-primate lentiviruses also include feline immunodeficiency virus (FIV) (see, Clements & Zink (1996) *Clinical Microbiology Reviews* 9, 100–117), which only infects felines. Numerous strains of FIV have been identified.

Non-primate (e.g., feline and ungulate) lentiviruses may provide a safer alternative than primate lentiviral vectors, but their use is complicated by a relative lack of knowledge about their molecular properties, especially their adaptability to non-host animal cells (Emerman, id). All lentiviruses display highly restricted tropisms (see, Clements & Zink (1996), supra, and Haase (1994) *Annals of the New York Academy of Sciences* 724, 75–86).

FIV was discovered in 1986 as a cause of acquired immune deficiency and neurological disease in, and only in, domestic cats (Felis catus) Pedersen et al. (1987) *Science* 235, 790–793 (1987); Elder & Phillips (1993) *Infectious Agents and Disease* 2, 361–374; Pedersen (1993) "The feline immunodeficiency virus" in The Retroviridae (ed. Levy, J. A.) 181–228 (Plenum Press, New York Bendinelli et al. (1995) *Clinical Microbiology Reviews* 8, 87–112; and, Sparger (1993) *Veterinary Clinics of North America, Small Animal Practice* 23, 173–191). In the great cats, FIV is widely dispersed geographically and appears to be commensal: 18 of 37 species of free-roaming, non-domestic Felidae are known to be infected world-wide, but none develop disease (Elder & Phillips (1993), supra; Olmsted et al. (1992) *Journal of Virology* 66, 6008–6018; Barr et al. (1995) *Journal of Virology* 69, 7371–7374; Courchamp & Pontier (1994) "Feline immunodeficiency virus: an epidemiological review." *Comptes Rendus de L Academie des Sciences. Serie III, Sciences de la Vie* 317, 1123–1134). The virus is prevalent, infecting 2–20% of domestic cat populations in North America, Europe and Japan; higher rates are seen in cats brought to veterinary attention (Pedersen (1993), supra and Courchamp, F. & Pontier (1994), supra). The worldwide prevalence of FIV in diverse Felidae and the observation that *Felis catus* sera dating to the 1960's show similar high rates of positivity, suggest that FIV has not been recently introduced into domestic cats (Bendinelli et al. (1995), supra, Olmsted et al. (1992), supra; Courchamp, F. & Pontier (1994) supra; Shelton et al. (1990) *Journal of Acquired Immune Deficiency Syndromes* 3, 623–630; Bennett & Smyth (1992) *British Veterinary Journal* 148, 399–412; Brown et al. (1993) *Journal of Zoo and Wildlife Medicine* 24, 357–364; Carpenter & O'Brien (1995) *Current Opinion in Genetics and Development* 5, 739–745.

There is no evidence for FIV infection of non-felids. Cross-infection by any of the ungulate or feline lentiviruses has never been observed in non-ungulates, or non-felids respectively. HIV and FIV differ notably in their modes of transmission since FIV is spread principally by biting (Pederson (1993), supra). Despite frequent exposure of humans to FIV through bites by domestic cats, this plausibly efficient means of inoculation does not result in human seroconversion or any other detectable evidence of human infection or disease (Pedersen (1993) id.; Bendinelli et al. (1995) supra.; Sparger (1993), supra; Courchamp, F. & Pontier (1994), supra; Brown et al. (1993).

FIV is also genetically and antigenically distant from the primate lentiviruses. Nucleotide sequence comparisons indicate a closer relationship to the ungulate lentiviruses than to HIV and SIV (Olmsted et al. (1989) *Proceedings of the National Academy of Sciences of the United States of America* 86, 2448–2452 (Olmsted et al. (1989) A); Olmsted et al. (1989) *Proceedings of the National Academy of Sciences of the United States of America* 86, 8088–8092 (Olmstead et al. (1989) B). Serological cross reactivity of FIV core proteins to several ungulate lentiviruses has been observed but none occurs to HIV-1, HIV-2 or SIV (Elder, J. H. & Phillips (1993), supra; Bennett, M. & Smyth (1992), supra; Olmsted et al. (1989) A, supra; Talbott et al. (1989) *Proceedings of the National Academy of Sciences of the United States of America* 86, 5743–5747; Miyazawa et al. (1994) *Archives of Virology* 134, 221–234). The virus encodes a dUTPase; this fifth pol-encoded enzymatic activity is a feature found only in non-primate lentiviruses (Wagaman et al. (1993) *Virology* 196, 451–457). Phylogenetic and epidemiologic data suggest an ancient adaptive episode between FIV and ancestors of wild felines as well as early evolutionary divergence from ancestors of other lentiviruses (Olmsted, R. A. et al. (1992), supra; Brown et al. (1993), supra; Carpenter & O'Brien (1995) Talbott et al. (1989), supra.).

At the cellular level, restrictions in human cells to both the productive and infective stages of the non-primate lentivirus life cycles are also evident (Tomonaga et al. (1994) *Journal of Veterinary Medical Science* 56, 199–201; Miyazawa et al. (1992) *Journal of General Virology* 73, 1543–1546; Thormar & Sigurdardottir (1962) *Acta Pathol Microbiol Scandinav* 55, 180–186; Gilden et al. (1981) *Archives of Virology* 67, 181–185; Carey & Dalziel (1993) *British Veterinary Journal* 149, 437–454. The bases for these blocks, which might impede development of non-primate lentivirus-based vectors for human application, are not well understood.

The CD4 molecules of primates are the only known lentivirus primary receptors (e.g., for HIV). Neither primary nor secondary receptors have previously been determined for any of the non-primate lentiviruses. Although an antibody that binds to the feline homologue of CD9 inhibits FIV infection in tissue culture (Willett (1994) *Immunology* 81, 228–233), subsequent investigation has established that neither CD9 nor the feline homologue of CD4 are FIV receptors (Willett et al. (1997) *Journal of General Virology* 78, 611–618). Reported obstacles to FIV expression in human cells have included poor function of core viral functions such as the Rev/RRE regulatory axis (Tomonaga, K. et al. (1994) supra; Simon et al. (1995) *Journal of Virology* 69, 4166–4172) and poor promoter activity of the long terminal repeat (LTR) (Miyazawa et al. (1992), supra; Sparger et al. (1992) *Virology* 187, 165–177. Because of these blocks, expression of the non-primate lentivirus Rev-dependent structural proteins in non-host animal cells has received very limited study.

In addition to the question of restricted tropism, production of non-primate lentivirus vectors in ungulate or feline cells for clinical use would create hazards for transmission of endogenous retroviruses or other potential pathogens. This risk has been documented for cells of diverse animal origin (Stoye & Coffin (1995) *Nature Medicine* 1, 1100; van der Kuyl et al. (1997) *Journal of Virology* 71, 3666–3676). Feline cells also contain multiple copies of a replication-competent, type C endogenous retrovirus (RD114) that replicates in human cells, phenotypically mixes with other retroviruses, and is related at the nucleotide sequence level to a primate retrovirus (baboon endogenous virus) (McAllister et al (1972) *Nature New Biol* 235, 3–6). Moreover, unlike most other type C mammalian retroviruses, RD114 resists inactivation by human serum complement (Takeuchi et al. (1994) *Journal of Virology* 68, 8001–8007). Cat cells may also contain other unknown and potentially pathogenic infectious agents.

Accordingly, there is a need in the art for safer lentiviral vectors, e.g., for the delivery of genes, cancer therapeutics, viral inhibitors and the like to non-dividing cells, including hematopoietic stem cells and neuronal cells, and for human vector packaging cells capable of packaging non-primate lentiviral vectors. The present invention provides these and other features.

SUMMARY OF THE INVENTION

This invention describes retroviral packaging systems, vectors, packagable nucleic acids and other features based on the discovery and design of non-primate lentiviral vectors which are active in human cells. The vectors, which are packageable by a non-primate lentivirus such as FIV, transduce non-dividing human cells. The packaging systems produce vector packaging components in trans in human cells, thereby avoiding the possibility of introducing new pathogens into the human population. These vectors and packaging components are useful for construction of general gene transfer vectors and for human gene therapy.

One class of retroviral vector provided by the invention has a vector nucleic acid packaged by a non-primate letivirus, such as FIV or an ungulate retrovirus. Thus the vector has a packagable nucleic acid which is recognized and packaged by the viral packaging proteins encoded by the selected retrovirus (e.g., FIV). The vector nucleic acid also includes a heterologous target nucleic acid such as a therapeutic gene. The vector nucleic acid is not virulent, because the nucleic acid lacks, or is defective, for one or more gene necessary for viral replication. However, when the missing or defective component (e.g., a retroviral protein) is provided in trans (e.g., in a packaging cell) the vector nucleic acid is packaged in a retroviral viral particle. The vectors optionally include vector packaging or replication elements such as viral proteins, viral particles, reverse transcriptase activity, or the like.

One preferred class of targets for the vectors of the invention are human cells, particularly non-dividing cells such as terminally differentiated hematopoietic cells and neurons (the cells are in vitro or in vivo). Accordingly, features directed to transduction and infection of human cells are preferred features. For example, incorporation of vesicular stomatitis virus (VSV) glycoprotein on the surface of the vector is preferred in some embodiments, as this facilitates entry of the vector into a variety of human cells. Similarly, incorporation of a promoter (e.g., the CMV promoter or a t-RNA promoter) which directs expression of one or more nucleic acid encoded by the vector in a human cell is desirable for production of nucleic acids and, optionally, proteins encoded by the vector in a human target cell.

Packaging plasmids which encode viral components which package the vector nucleic acids in trans are also provided. The packaging plasmids include a promoter which is active in a human cell (i.e., a human cell used for vector packaging). This promoter is operably linked to a nucleic acid encoding at least one protein necessary for packaging the vector nucleic acid, e.g., an FIV or other non-primate lentivirus packaging nucleic acid. The packaging plasmid lacks an FIV packaging site.

In one preferred embodiment, the packaging plasmid has an FIV LTR having a U3 promoter deletion, typically with a heterologous promoter insertion into the deletion site. This arrangement results in eliminating endogenous FIV LTR promoter function and permitting regulation by the heterologous promoter.

It will be appreciated that retroviral packaging cells which package non-primate lentiviral packagable nucleic acids are provided by the packaging plasmids described above. In particular, the cells, which are preferably human, comprise packaging plasmids encoding necessary viral packaging elements (e.g., Gag and Env proteins). These packaging elements are used to package packageable vector nucleic acids in trans. For safety reasons, it is often preferable for the cell to include separate packaging plasmids, each of which encode different packaging proteins. For example, a packaging cell can include two separate packaging plasmids encoding distinct retroviral packaging proteins (e.g., FIV Gag and Env proteins). The cell can further comprise a plasmid which encodes a pseudotyping element such as the VSV envelope glycoprotein to expand the range of any packaged plasmid. The psudotyping element can be encoded on the same plasmid as other non-primate retroviral elements, or on a separate plasmid. In any case, desired packaging elements are under the control of suitable regulatory elements which direct expression of the components in a human cell. It will be appreciated that packageble nucleic acids (e.g., which include an FIV packaging site and a heterologous nucleic acid) are optionally transduced (stably or transiently) into the cells of the invention.

DEFINITIONS

Figure 1:
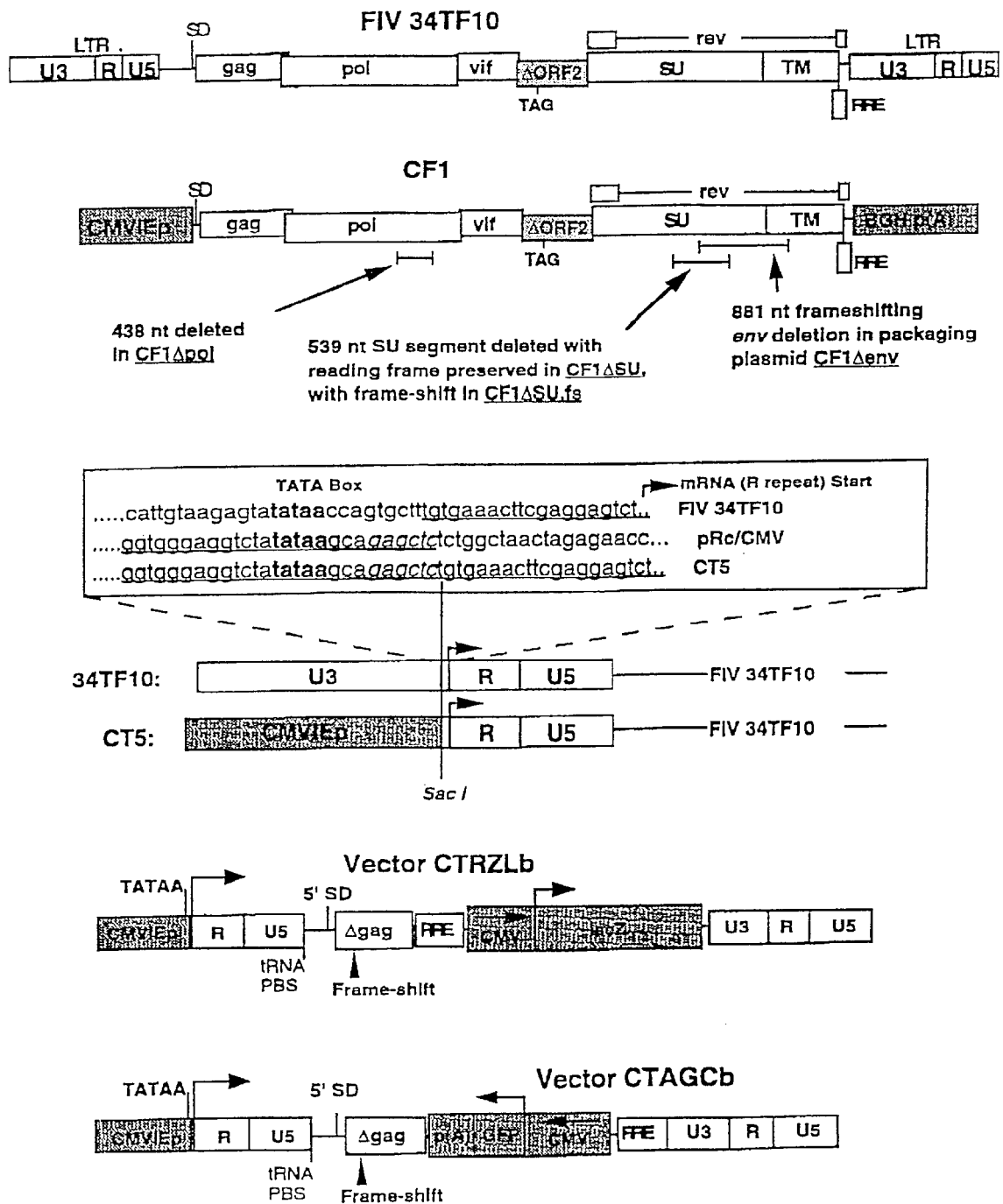
FIG. 1 is a schematic describing nucleic acid constructs of the invention, including FIV34TF-10, CT5, CTRZLb and CTAGCb (SEQ ID NOS: 1–3).

For purposes of the present invention, the following terms are defined below.

A "vector" is a composition which can transduce, transform or infect a cell, thereby causing the cell to express vector encoded nucleic acids and, optionally, proteins other than those native to the cell, or in a manner not native to the cell. A vector includes a nucleic acid (ordinarily RNA or DNA) to be expressed by the cell (a "vector nucleic acid"). A vector optionally includes materials to aid in achieving entry of the nucleic acid into the cell, such as a retroviral particle, liposome, protein coating or the like.

A "non-primate lentivirus packageable nucleic acid" is a nucleic acid having a functional virus packaging site from an ungulate lentivirus or FIV lentivirus. Nucleic acids having this packaging site which can be incorporated into a viral particle by viral components supplied in trans by a corresponding wild-type virus are packaged by the wild-type virus (or appropriate packaging components derived from a wild-type virus).

A "packaging defect which blocks self packaging" of a non-primate lentiviral vector nucleic acid is an inability of the nucleic acid to produce at least one viral protein necessary for packaging the vector nucleic acid into a viral particle in the context of a cell. For example, when Gag or Env proteins are not encoded by the lentiviral vector, the proteins must be supplied in trans before the vector nucleic acid can be packaged in the cell. The omission can be a deletion or mutation of a gene necessary for viral packaging from a viral clone, in the coding or non-coding (e.g., promoter) region of the relevant gene. The vector nucleic acid is trans-rescuable when it encodes a viral packaging site which is recognized be a non-primate lentiviral vector such as FIV.

A "packaging plasmid" is a plasmid which encodes components necessary for production of viral particles by a cell transduced by the packaging plasmid. The packaging plasmid optionally encodes all of the components necessary for production of viral particles, or optionally includes a subset of the components necessary for packaging. For instance, in one preferred embodiment, a packaging cell is transformed with more than one packaging plasmid, each of which has a complementary role in the production of a non-primate lentiviral particle (e.g., for FIV). The packaging plasmid lacks a functional packaging site, i.e., a packaging site recognized by the non-primate lentivirus components encoded by the plasmid, rendering the plasmid incapable of self packaging.

Two (or more) non-primate lentivirus based packaging plasmids are "complementary" when they together encode all of the functions necessary for viral packaging, and when each individually does not encode all of the functions necessary for packaging. Thus, e.g., when two plasmids transduce a single cell and together they encode the information for production of FIV packaging particles, the two vectors are "complementary." The use of complementary plasmids is preferred because it increases the safety of any packaging cell made by transformation with a packaging plasmid by reducing the possibility that a recombination event will produce an infective virus.

Packaging plasmids encode components of a viral particle. The particles are competent to package target RNA which has a corresponding packaging site. "High efficiency packaging plasmids" package target RNAs having packaging sites such that packaging cells transiently or stably transduced with the packaging plasmid and transduced with a target packageable nucleic acid target packageable vector RNA at a titer of at least about $10^5$ or $10^6$ to about $10^7$ or even $10^8$ transducing units per ml or more. The precise titer which is produced varies depending on the nature of the packageable nucleic acid and the packaging cell selected. Higher infectivities are typically obtained when packaging vectors with complete packaging sites.

An "inhibitor" or "viral inhibitor" is most typically a nucleic acid which encodes an active anti-viral agent, or is itself an anti-viral agent. Thus, in one class of embodiments, the inhibitor is a "direct inhibitor," i.e., the inhibitor acts directly on a viral component to inhibit the infection, replication, integration or growth of the virus in the cell. For instance, in one particularly preferred embodiment, the inhibitor comprises a trans-active ribozyme which cleaves an HIV transcript. In this configuration, the inhibitor is typically an RNA molecule with catalytic nuclease activity. In another class of embodiments, the inhibitor is an "indirect inhibitor," i.e., the inhibitor encodes the direct inhibitor. An inhibitor "encodes" a direct inhibitor such as an active ribozyme, protein, RNA molecular decoy, or anti-sense RNA if it contains either the sense or anti-sense coding or complementary nucleic acid which corresponds to the direct inhibitor. By convention, direct inhibitor RNAs such as ribozymes are typically listed as their corresponding DNA sequences. This is done to simplify visualization of the corresponding active RNA, which is equivalent to the given sequence with the T residues replaced by U residues.

"Viral inhibition" refers to the ability of a component to inhibit the infection, growth, integration, or replication of a virus in a cell. Inhibition is typically measured by monitoring changes in a cell's viral load (i.e., the number of viruses and/or viral proteins or nucleic acids present in the cell, cell culture, or organism) or by monitoring resistance by a cell, cell culture, or organism to infection.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A "constitutive" promoter is a promoter which is active under most environmental and developmental conditions. An "inducible" promoter is a promoter which is under environmental or developmental regulation.

The terms "isolated" or "biologically pure" refer to material which is substantially or essentially free from components which normally accompany it as found in its native state.

The term "heterologous" when used with reference to portions of a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene, such as an anti-viral ribozyme. Thus, with reference to the ribozyme coding sequence, the promoter is heterologous.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA). A "comparison window", as used herein, refers to a segment of at least about 50 contiguous positions, usually about 50 to about 200, more usually about 100 to about 150 in which a sequence is compared to a reference sequence of the same number of contiguous positions after the two sequences are optimally aligned. Methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment. "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) *Proteins* W.H. Freeman and Company. Finally, the addition of sequences which do not alter the activity of a nucleic acid molecule, such as a non-functional sequence is a conservative modification of the basic nucleic acid.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

An "FIV-1 Gag protein" is a protein encoded by the FIV-1 gag gene. The Gag proteins are typically translated as a large preprotein which is cleaved to form the structural core proteins which package wild-type FIV genomic RNA. A truncated Gag protein is a protein produced from a gag gene having a deletion relative to the wild-type sequence. Similarly, an FIV reverse transcriptase protein and an FIV envelope protein are encoded by the pol and env genes, respectively.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means.

A "recombinant expression cassette" or simply an "expression cassette" is a nucleic acid construct, generated recombinantly or synthetically, with nucleic acid elements which permit transcription of a particular nucleic acid in a cell. The recombinant expression cassette can be part of a plasmid, virus, or nucleic acid fragment. Typically, the recombinant expression cassette includes a nucleic acid to be transcribed, and a promoter. In some embodiments, the expression cassette also includes, e.g., an origin of replication, and/or chromosome integration elements (e.g., a retroviral LTR).

The term "subsequence" in the context of a particular nucleic acid sequence refers to a region of the nucleic acid equal to or smaller than the specified nucleic acid.

A virus or vector "transduces" a cell when it transfers nucleic acid into the cell. A virus or vector is "infective" when it transduces a cell, replicates, and (without the benefit of any complementary virus or vector) spreads progeny vectors or viruses of the same type as the original transducing virus or vector to other cells in an organism or cell culture, wherein the progeny vectors or viruses have the same ability to reproduce and spread throughout the organism or cell culture. Thus, for example, a nucleic acid encoding an FIV particle is not infective if the nucleic acid cannot be packaged by the FIV particle (e.g., if the nucleic acid lacks an FIV packaging site), even though the nucleic acid can be used to transfect and transform a cell. Similarly, an FIV-packageable nucleic acid packaged by an FIV particle is not infective if it does not encode the FIV particle that it is packaged in, even though it may be used to transform and transfect a cell. Vectors which do not encode a complete set of viral packaging components (e.g., Gag and Env proteins) are "packaging deficient." These vectors are "trans-rescuable" when the vectors are packaged by viral proteins supplied in trans in a packaging cell. If an FIV-packageable nucleic acid is used to transform a cell infected with FIV in a cell culture or organism infected with FIV, the FIV-packageable nucleic acid will be replicated and disseminated throughout the organism in concert with the infecting FIV virus. However, the FIV-packageable nucleic acid is not itself "infective", because packaging functions are supplied by the infective FIV virus via trans complementation.

A cell "supernatant" is the culture medium in which a cell is grown. The culture medium includes material from the cell, including, e.g., FIV viral particles which bud off from the cell membrane and enter the culture medium.

DETAILED DISCUSSION OF THE INVENTION

Transfection of the non-primate lentiviral clone CF1 into human HeLa, 293 and 293-T kidney cells by the calcium phosphate co-precipitation method produced the surprising result of widespread ballooning syncytia (multi-nucleated giant cells produced by fusion of envelope-expressing cells with other cells) containing fifty to several hundred nuclei and high levels (over one million cpm) of supernatant reverse transcriptase. Unexpectedly, human 293 and 293-T cell and HeLa monolayer cultures were reproducibly 90–95% destroyed by syncytia after transient transfection of CF1 (for example by transfection of 10 μg of CF1 in a 75 cm$^2$ flask), yet, no infectious or replication-competent virus was produced: transfer of large volumes of CF1-transfected 293-T cell supernatant to fresh 293 or 293-T cells or to Crandall feline kidney cells resulted in no syncytia or RT production. CF1Δenv, which is identical to CF1 except for an FIV envelope deletion does not cause syncytia but does produce high levels of reverse transcriptase and of viral functions needed for packaging of vectors. These unprecedented results produced the novel insight that all the functions of non-primate vectors such as FIV needed for protein production, including the Rev/RRE axis of regulation, FIV gag/pol production and envelope-mediated syncytia, could take place in human cells if the FIV promoter were replaced with a promoter active in human cells.

Accordingly, this invention provides the first use of non-primate lentiviral vectors packaged in human packaging cells for transduction of human target cells. Prior to the present invention there was no way of knowing whether these packaging systems could be developed in human cells, or whether packaged non-primate lentiviral vectors could be used to transduce human cells, or whether the regulatory, processing and packaging components of such vectors would be active in human cells. There was no information on desirable arrangements or particular constructs especially useful in the vectors and packaging cells of the invention, e.g., the arrangement and construction of FIV based vectors and packaging systems described herein. Advantages to the vectors include a lack of human pathogenicity for the viruses that the vectors and packaging systems are based upon and the ability of the vectors to transduce non-dividing cells human cells. Such non-dividing cells include, but are not limited to, cells of the human nervous system, eye, hematopoietic system, integument, endocrine system, hepatobiliary system, gastrointestinal tract, genitourinary tract, bone, muscle, cardiovascular system and respiratory system. All of these cells are transduced in vitro or in vivo using the vectors of the invention. These vectors also prevent exposure of patients to non-human cells and prevent exposure to lentiviral genes or lentiviral proteins derived from known pathogens.

The mechanisms of the FIV life cycle in human cells are described herein. It is reported here for the first time that Feline immunodeficiency virus (FIV) proteins encoded by a packaging plasmid can be expressed at high levels in human cells, in replication-defective fashion, and supplied to FIV packagable vectors in trans, by replacing the long terminal repeat of the FIV genome with a heterologous promoter such as the human cytomegalovirus immediate early promoter (CMV promoter). In particular, substitution of a heterologous polI II promoter for the promoter elements of the FIV LTR enabled high-level FIV protein production, in trans, in human cells. In addition, selectively replacing the FIV 5-prime U3 element by precisely fusing a heterologous promoter to the R repeat resulted in high production in human cells of wild type FIV that was replication-competent only in feline cells. A three plasmid, replication-defective, env-deleted, fully heterologously-promoted FIV vector system was constructed and found to efficiently transduce dividing and non-dividing human cells with vesicular stomatitis virus glycoprotein G (VSV-G)-pseudotyped FIV particles. There was no transduction advantage to feline cells; relative transduction efficiencies in dividing cells of diverse human and feline lineages were the same as for a Moloney murine leukemia virus (M-MuLV)-based vector. In distinct contrast to the common M-MuLV vector, FIV vectors efficiently transduced non-dividing human cells, including terminally differentiated human macrophages and neurons (hNT neurons). Extensive syncytia form when FIV expression is enabled in human cells; this activity requires expression of CXCR4/fusin35, the co-receptor for syncytium-inducing HIV isolates. Expression of human CXCR4 in feline CRFK cells changes viral phenotype to highly syncytium-inducing and mediates FIV-enveloped vector entry. The studies show that FIV can utilize the human homologue of CXCR4 for syncytiagenesis in human, rodent, and feline cells and, consistent with a co-receptor role, for viral entry in feline cells.

Feline immunodeficiency virus that is replication-competent for feline cells but not human cells is produced at high levels in human and feline cells by a precise fusion of a heterologous promoter such as the human cytomegalovirus immediate early promoter (CMV promoter) and the FIV genome immediately upstream of the FIV R repeat as described. In one embodiment, the fusion is joined precisely over the TATA box (the TATA box of the CMV promoter is used; FIV sequences begin at the Sac I site just downstream of the TATA box). Details of this fusion, which preserves TATA Box to mRNA transcriptional start site spatial arrangements, are diagrammed in the examples.

FIV-derived retroviral vectors are optionally expressed at high levels from the same heterologous promoter-R repeat fusion in which the five-prime U3 element of the FIV vector has been precisely replaced by a heterologous promoter. These FIV vectors can be delivered at high titer in replication-defective fashion to non-feline mammalian cells, including both dividing and growth-arrested human cells, via heterologous envelopes, including but not limited to pseudotyping by the vesicular stomatitis virus envelope glycoprotein G (VSV-G); this is the first demonstration of delivery of genes to human cells using a non-primate lentivirus.

Co-production of FIV proteins and FIV vectors resulted in high titer, replication-defective lentiviral vectors that can deliver genes to human cells as well as feline cells. FIV vector titers exceeding $10^7$ per ml on human cells were achieved and higher titers are achieved with refinements of production and concentration using available methods. Therefore, the invention has direct applicability to human gene therapy. Other promoters active in human cells will also be useful in some embodiments.

The invention embodies several safety advantages. One important safety advantage of this invention is production of the replication-defective vector entirely in human cells. The native FIV promoter (LTR) is inactive or minimally active in human cells. In fact, the hCMVIE promoter as implemented here permits higher expression than the FIV LTR in feline as well as human cells. While the native FIV LTR is used in feline producer cells to drive expression (analogously to the use of the Moloney murine leukemia (MoMLV) virus promoter in MoMLV-based systems), such use presents distinct safety problems that are preferably avoided. Feline cells can contain a replication-competent type C endogenous retrovirus (RD114) that replicates in human cells. Feline cells, which have received less scientific study that human cells, may also contain other unknown infectious agents that are potentially pathogenic. RD114 was originally isolated from human rhabdomyosarcoma cells that had been passaged in fetal kittens; replication-competent RD114 has also been isolated from cultured feline cell lines by co-cultivation with human and other non-feline cells. In addition, RD144 is strikingly related at the nucleotide sequence level to a primate retrovirus (baboon endogenous virus or BaEV); this fact, in addition to demonstrated replication competence in human cell lines, suggests clear potential for cross-species transmission to humans. The danger of transmission of endogenous retroviruses such as RD114 or other viruses to humans through xenotransplantation or exposure to biological materials derived from animal cells or tissues has recently generated great concern. Pig cells, for example, have now been shown to harbor an endogenous retrovirus that can replicate in human cells similarly to RD114; this finding is now considered by experts in the field to raise serious doubts about the safety of animal organ xenotransplantation into humans or use for therapeutic purposes of animal-derived biologicals that are not sterilizable. Therefore, exposure of humans to vectors derived from feline or ungulate cell lines, which are far less well characterized than human or rodent cell lines, would be problematic. The chimeric design of the vectors herein permits production entirely in well-defined human producer cell lines such as 293T cells. The safety advantage is avoidance of exposure at any stage of production to feline cells or tissues. Accordingly, for applications involving introduction of cells or vectors to patients, it is preferable to use vectors packaged in human packaging cells.

In all its embodiments, the system also represents a significant safety advance over HIV-based lentiviral vectors because, as noted above, FIV is neither transmissible to humans nor pathogenic in humans. This invention therefore makes use of the well-documented fact that no evidence for pathogenicity of FIV in humans exists. The practical applicability of this invention also benefits from the fact that lack of tropism or pathogenicity in humans is better established for FIV than for any other non-primate lentivirus (these include Visna/Maedi, CAEV, EIAV and BIV) because many thousands of humans are exposed yearly by the same means by which FIV is predominantly transmitted among both feral and domestic cats in nature, i.e., cat bites.

All lentiviruses are transmitted exclusively by exchange of body fluids. HIV is predominantly sexually transmitted; there is little evidence that FIV is sexually transmitted in nature; instead, cat bites—which humans are also commonly exposed to—are the main mechanism. Bite wounds are common among cats because these animals are territorial and males in particular engage in frequent fights over territory and dominance; FIV infection is accordingly more common among male cats than among female cats.

In summary, there is no evidence for FIV infection of non-felids: this restricted tropism is characteristic of all known lentiviruses. Biting is the major natural means of spread of FIV between cats and despite frequent exposure of humans to FIV by cat bites, this plausibly efficient means of inoculation does not result in human seroconversion or any other detectable evidence of human infection. Among the non-primate lentiviruses, therefore, epidemiological evidence against human pathogenicity is compelling for FIV.

Since FIV is routinely worked with using Biosafety Level-2 (BL-2) practices, vectors can be routinely worked with in BL-2 facilities, risks posed to personnel involved in their development and production are lessened compared to HIV vectors, and ease and convenience of production is enhanced.

In addition to the safety advantages inherent in using a non-primate lentivirus for cellular gene transfer and gene therapy, a preferred system described herein from a molecular clone of FIV (34TF10) is defective in an important FIV gene (ORF2) and is therefore an attenuated virus. 34TF10 replicates in adherent cat cell lines but not in lymphocytes; replication-competence in feline lymphocytes has been mapped to ORF2. In addition, the ORF2-minus virus is neural tropic. If needed for delivery to certain cell types, ORF2 can be repaired. In addition, in other embodiments, other strains or molecular clones of FIV are used in a similar fashion since the present invention makes apparent their adaptability to transduction of human cells.

Although a chimeric construction fusing the heterologous promoter to FIV sequences was used in one example herein, because the fusion is located at the start of transcription, only FIV sequences are transcribed (i.e., only FIV promoter sequences appear in the mRNA generated by the system; the heterologous promoter sequences are not transcribed). The possibility of a replication-competent chimeric virus arising by RNA-level recombination is therefore reduced.

In addition, since this lentivirus that is phylogenetically distant from HIV is now shown in the present invention to be adaptable to transduction of human cells, it is now clear that other non-primate lentiviruses, particularly the ungulate lentiviruses, can be similarly utilized.

By engineering expression from the packaging plasmid, the vector and the envelope expression plasmid occur from the same human promoter, synchronized expression (i.e., temporal coordination) of protein expression is facilitated.

Making Packaging Plasmids and Packageable Nucleic Acids

The present invention provides a variety of packaging plasmids and packageable nucleic acids as described supra. Packaging plasmids include non-primate lentiviral derived nucleic acids, particularly those derived from FIV and the ungulate lentiviruses. Packageable nucleic acid vectors encode RNAs which comprise a lentiviral packaging site (e.g., FIV or ungulate derived), and optionally comprise other non-primate lentiviral nucleic acids, or heterologous nucleic acids.

The packagable vectors and packaging plasmids of the invention are derived from lentiviral clones. Many such clones are known to persons of skill, and publicly available. Well-established repositories of sequence information include GenBank, EMBL, DDBJ and the NCBI. Well characterized HIV clones include: HIV-$1_{NL43}$, HIV-$1_{SF2}$, HIV-$1_{BRU}$, HIV-$1_{MN}$.

Furthermore, viral clones can be isolated from wild-type viruses using known techniques. Typically, a lambda-phage clone, containing a full-length lentiviral provirus, is obtained from the genomic DNA of a cell line infected with a viral strain isolated from the peripheral blood mononuclear cells of a seropositive animal. The virus is replication competent in vitro, producing infectious progeny virions after direct transfection into target cells from the organism (e.g., $CD4^+$ cells). In general, a complete virulent genome can be used to make a packaging plasmid. A "full-length FIV genome" in relation to an FIV packaging vector consists of a nucleic acid (RNA or DNA) encoded by an FIV virus or viral clone (e.g., a DNA phage) which includes the 5' and 3' LTR regions and the genes between the LTR regions which are present in a typical corresponding virus. For FIV, these genes include: gag-pol, env and orf-2, and in addition there are several uncharacterized reading frames, particularly in env.

A packaging plasmid is made by deleting the packaging site from a full-length genome, rendering the clone capable of producing viral proteins, but incapable of self packaging viral RNAs. The RNA secondary structure of the FIV packaging site likely includes the region between MSD and gag-pol; in addition, other regions may be important for proper packaging. The precise nature of the packaging site can be determined by performing deletion analysis.

In packaging plasmids, preferably, the entire psi site (packaging site) is deleted, but any mutation or deletion which deletes or mutates enough of the site to inhibit packaging is sufficient. This typically results in a substantial deletion in the region between the major splice donor site ("MSD") and the beginning of the gag gene, and may include other regions as well. Deletion of promoter elements which direct viral expression of the encoded viral proteins is also desirable, as is incorporation of heterologous promoters. In particular, human promoters (i.e., promoters active in human cells which are typically, but not necessarily, of human origin, or derived from a human pathogen such as a virus which is active in a human).

The resulting packaging plasmids of the invention are used to make viral particles, by transducing the deletion clone into a packaging cell (typically a human cell such as a 293 or other well-characterized cell which does not comprise any unwanted components) and expressing the plasmid. Because the plasmids lack a lentiviral packaging site, they are not packaged into viral particles.

To increase the safety of the transduced packaging cells, it is preferable to cut (e.g., by subcloning) the packaging plasmid (or homologous clones) into multiple packaging plasmids with complementary functions. This decreases the chances that a recombination event will result in an infectious particle.

Packageable nucleic acids encode an RNA which is competent to be packaged by an FIV particle. Such nucleic acids can be constructed by recombinantly combining an FIV packaging site with a nucleic acid of choice. The packaging site (psi site) is located adjacent to the 5' LTR, primarily between the MSD site and the gag initiator codon (AUG) in the leader sequence of the gag gene. Thus, the minimal packaging site includes a majority of nucleic acids between the MSD and the gag initiator codon from the relevant lentivirus. Preferably, a complete packaging site includes sequences from the 5' LTR and the 5' region of gag gene for maximal packaging efficiency. These packaging sequences typically include a portion of the gag gene, e.g., extending about 100 bases into the coding region of gag or further, and about 100 bases into the FIV 5' LTR or further. In addition, sequences from the env gene are optionally included in the packaging site, particularly the RRE.

Given the strategy for making the packaging plasmids and target packageable vector nucleic acids of the present invention, one of skill can construct a variety of clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426, 039.

Oligonucleotides for use as probes, e.g., in in vitro amplification methods, for use as gene probes, or as inhibitor components (e.g., ribozymes) are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) Nucleic Acids Res., 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

Making Conservative Substitutions

One of skill will appreciate that many conservative variations of the nucleic acid constructs disclosed yield a functionally identical construct. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties (see, the definitions section, supra), are also readily identified as being highly similar to a disclosed construct. Such conservatively substituted variations of each explicitly disclosed sequence are a feature of the present invention.

One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) Gene 8:81–97, Roberts et al. (1987) *Nature* 328:731–734 and Sambrook, Innis, Ausbel, Berger, Needham VanDevanter and Mullis (all supra).

One of skill can select a desired nucleic acid of the invention based upon the sequences provided and upon knowledge in the art regarding retroviruses generally. The specific effects of many mutations in retroviral genomes are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplar conservative amino acid substitutions.

Finally, most modifications to nucleic acids are evaluated by routine screening techniques in suitable assays for the desired characteristic. For instance, changes in the immunological character of encoded polypeptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Making Stable Packaging Cell Lines

Stable packaging cell lines are made by stably or transiently transducing a mammalian cell with a packaging plasmid, most preferably by transducing a human cell. The transduction of mammalian (including human) cells is known in the art. Host cells are competent or rendered competent for transformation by various known means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells.

Transformed cells are cultured by means well known in the art. See, also Kuchler et al. (1977) *Biochemical Methods in Cell Culture and Virology*, Kuchler, R. J., Dowden, Hutchinson and Ross, Inc. Mammalian cell systems often will be in the form of monolayers of cells, although mammalian cell suspensions are also used. Illustrative examples of mammalian cell lines include VERO and HeLa cells, 293 embryonic kidney cells, Chinese hamster ovary (CHO) cell lines, W138, BHK, Cos-7 or MDCK cell lines (see, e.g., Freshney, supra). Human cells are most preferred.

Supernatants from cell cultures of the packaging cells of the invention are obtained using standard techniques such as those taught in Freshney, supra. See also, Corbeau et al. (1996) *Proc. Natl. Acad. Sci. USA* 93:14070–14075 and the references therein. Components from the cell supernatants can be further purified using standard techniques. For example, FIV particles in the supernatant can be purified from the supernatant by methods typically used for viral purification such as centrifugation, chromatography, affinity purification procedures, and the like.

Transforming mammalian cells with nucleic acids can involve, for example, incubating competent cells with a plasmid containing nucleic acids which code for an FIV particle. The plasmid which is used to transform the host cell preferably contains nucleic acid sequences to initiate transcription and sequences to control the translation of the encoded sequences. These sequences are referred to generally as expression control sequences. Illustrative mammalian expression control sequences are obtained from the SV-40 promoter (*Science* (1983) 222:524–527), the CMV I.E. Promoter (*Proc. Natl. Acad. Sci.* (1984) 81:659–663), the CMV promoter, or the metallothionein promoter (*Nature* (1982) 296:39–42). A cloning vector containing expression control sequences is cleaved using restriction enzymes and adjusted in size as necessary or desirable and ligated with DNA coding for the HIV sequences of interest by means well known in the art. A huge variety of specific pol II and pol III promoters active in human cells are known in the art and one of skill is able to select and use such promoters based upon the desired expression level, pattern, transformed cell, or the like.

Polyadenlyation or transcription terminator sequences from known mammalian genes are typically incorporated into the vectors of the invention. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781). Additionally, gene sequences to control replication in a particular host cell are incorporated into the vector such as those found in bovine papilloma virus type-vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Va. pp. 213–238.

Co-plasmids can be used in selection methods. In these methods, a plasmid containing a selectable marker, such as an antibiotic resistance gene, is used to co-transfect a cell in conjunction with a plasmid encoding HIV packaging nucleic acids. The cells are selected for antibiotic resistance, and the presence of the plasmid of interest is confirmed by Southern analysis, northern analysis, or PCR. Co-plasmids encoding proteins to be expressed on the surface of an HIV particle (e.g., proteins which expand the host range of the capsid such as the VSV envelope, a cell receptor ligand, or an antibody to a cell receptor) are optionally transduced into the packaging cell. In addition to VSV, the envelope proteins of other lipid enveloped viruses are optionally incorporated into a particle of the invention, thereby expanding the transduction range of the particle.

Viral vectors containing nucleic acids which encode selected sequences are also used to transform cells within the host range of the vector. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein.

Once stable transformed cell lines are made which express FIV particles, the transformed cell lines are transfected with vectors which encode nucleic acids to be incorporated into the FIV vectors. Typically, these vectors are plasmids or are coded in viral vectors. The packaged nucleic acids include an FIV packaging site subsequence in conjunction with a sequence of interest, such as a viral inhibitor or other gene therapeutic (it will be appreciated that any condition which is mediated by non-dividing cells or their progeny are treatable using the vectors of the invention, including HIV infections, HTLV infections, lymphomas, leukemias, neural tumors and the like).

Human cells are preferred packaging cell lines, and can be made competent for transformation by the techniques described above. For example, to generate a stable FIV packaging cell line, FIV cells were transfected by the Calcium-Phosphate method as described in the examples herein. A subconfluent culture, e.g., in a 6-well plate (Costar, Cambridge, Mass.) is transfected with linearized and calcium-phosphate precipitated plasmid (10 µg), e.g., in Dulbecco's modified Eagle's medium supplemented with 10% FCS, antibiotics and glutamine (DMEM-10% FCS), optionally with a co-plasmid marker. After 18 hours, wells are washed with Dulbecco's phosphate-buffered saline (PBS) pH 7.8, incubated for 2 min. at 20° C. with 15% glycerol solution in HEPES-buffered saline (50 mM HEPES pH 7.1, 280 mM NaCl, 1.5 mM Na2HP04), washed twice with PBS and cultured in DMEM-10% FCS. The cells are subjected to selection as appropriate for a transduction marker gene.

Assaying for Packaging Plasmids, Packageable Nucleic Acids and FIV Particles in Packaging Cell Lines, Target Cells and Cell Lysates A wide variety of formats and labels are available and appropriate for detection of packaging plasmids, packageable nucleic acids and lentiviral particles in packaging cells, target cells, patients and cell lysates. Antibodies to lentiviral components, and the polypeptides and nucleic acids of the invention (vectors, packaging plasmids, encoded nucleic acids and polypeptides, etc.) are detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radio-immunoassays (RIAs), enzyme-linked immunosorbent assays (ELISAs), immunofluorescent assays, and the like. Several available ELISA assays for the detection of lentiviral components (e.g., FIV) are available, allowing one of skill to detect non-primate lentiviral particles, or non-primate lentiviral virus in a biological sample.

The detection of nucleic acids proceeds by well known methods such as Southern analysis, northern analysis, gel electrophoresis, PCR, radiolabeling and scintillation counting, and affinity chromatography. Many assay formats are appropriate, including those reviewed in Tijssen (1993) *Laboratory Techniques in biochemistry and molecular biology—hybridization with nucleic acid probes* parts I and II, Elsevier, New York and Choo (ed) (1994) *Methods In Molecular Biology Volume 33—In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization". A variety of automated solid-phase detection techniques are also appropriate. For instance, very large scale immobilized polymer arrays (VLSIPS™ are used for the detection of nucleic acids. See, Tijssen (supra), Fodor et al. (1991) *Science*, 251: 767–777 and Sheldon et al. (1993) *Clinical Chemistry* 39(4): 718–719. Finally, PCR is also routinely used to detect nucleic acids in biological samples (see, Innis, supra for a general description of PCR techniques).

In one preferred embodiment, antibodies are used to detect proteins expressed by the packaged vector, the packaging nucleic acid or to monitor circulating HIV, HTLV (or other relevant pathogen), levels in human blood, e.g., to monitor the in vivo effect of a gene therapeutic agent coded by the FIV packaged nucleic acids. In other embodiments, antibodies are co-expressed in the packaging cells to be incorporated into viral particles. Methods of producing polyclonal and monoclonal antibodies are known to those of skill in the art, and many antibodies are available. See, e.g., Coligan (1991) *Current Protocols in Immunology* Wiley/Greene, NY; and Harlow and Lane (1989) *Antibodies: A Laboratory Manual Cold Spring Harbor Press, NY; Stites et al. (eds.) Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 µM, preferably at least about 0.01 µM or better, and most typically and preferably, 0.001 µM or better.

Use of the Nucleic Acids of the Invention as Molecular Probes

In addition to their utility in making packaging cell lines, the non-infective packaging plasmids of the invention can be used to detect wild-type virus in biological samples using Southern or northern blot assays. In brief, a nucleic acid encoded by the packaging plasmid is labeled, typically using a radio or bioluminescent label, and used to probe a northern or Southern blot of a sample suspected of containing a virus (FIV, an ungulate retrovirus, etc.). The use of the packaging plasmid as a probe is safer than the use of an infective virus as a probe. The packaging plasmid is also more likely to detect a wild type virus than a smaller probe, because, unlike a small probe, the packaging plasmid probe optionally has virtually the entire genome in common with a wild-type virus (except for the packaging site), making it improbable that the wild type virus could escape detection by mutation of the probe binding site.

Furthermore, the packaging plasmid can be used as positive controls in essentially all known detection methods for the detection of the corresponding retrovirus (e.g., FIV). In this embodiment, a packaging plasmid nucleic acid or encoded polypeptide is used as a positive control to establish that an FIV detection assay is functioning properly. For instance, oligonucleotides are used as primers in PCR reactions to detect FIV nucleic acids in biological samples such as feline blood in veterinary settings. The packaging plasmid, which comprises nucleic acid subsequences corresponding to the region to be amplified is used as an amplification templates in a separate reaction from a test sample such as human blood to determine that the PCR reagents and hybridization conditions are appropriate. Similarly, the polypeptides encoded by the packaging plasmid can be used to check ELISA reagents in assays for the detection of FIV expression products in biological samples.

Packageable nucleic acids can also be used in the same fashion as molecular probes, e.g., when they encode HIV components such as HIV packaging sites, HIV LTRs, transdominant Tat or Rev proteins, or the like, for detection of HIV, or as HIV detection reagents.

Cellular Transformation and Gene Therapy

The present invention provides packageable nucleic acids for the transformation of cells in vitro and in vivo. These packageable nucleic acids are packaged in non-primate lentiviral particles such as FIV particles, in the lentiviral packaging cell lines described herein. Preferably, when the target is in the host range of the VSV virus (e.g., a hematopoietic stem cell) the particle also includes VSV glycoproteins. The nucleic acids are transfected into cells through the interaction of the FIV particle surrounding the nucleic acid and an FIV or VSV cellular receptor.

In one particularly preferred class of embodiments, the packageable nucleic acids of the invention are used in cell transformation procedures for gene therapy. Gene therapy provides methods for combating chronic infectious diseases such as HIV, as well as non-infectious diseases such as cancer and birth defects such as enzyme deficiencies. Yu et al. (1994) *Gene Therapy* 1:13–26 and the references therein provides a general guide to gene therapy strategies for HIV infection. See also, Sodoski et al. PCT/US91/04335. One general limitation of common gene therapy vectors such as murine retroviruses is that they only infect actively dividing cells, and they are generally non-specific. The present invention provides several features that allow one of skill to generate powerful retroviral gene therapy vectors which specifically target stem cells in vivo, and which transform many cell types in vitro. CD4$^+$ cells, neuronal cells and other non-dividing cells (often CXCR4 positive) are transduced by nucleic acids packaged in FIV particles. In addition, the vectors are optionally pseudotyped for transformation of stem cells.

Pseudotyping The Packageable Vector

Hematopoietic stem cells are particularly preferred targets for cell transformation in general, and for gene therapy (particularly anti-HIV gene therapy) in particular. Packageable vectors are made competent to transform CD34$^+$ cells by pseudotyping the vector. This is done by transducing the packaging cell line used to package the vector with a nucleic acid which encodes an Env protein which supplants or complements the retroviral env function. The envelope function can be supplied in trans by any number of heterologous viral envelope proteins. These include, but are not limited to, VSV-G, the amphotropic envelope of Moloney murine leukemia virus (MoMuLV), and gibbon ape leukemia virus (GALV) envelope. The vesicular stomatitis virus (VSV) envelope glycoprotein, which expressed on the surface of the vector is a preferred pseudotyping component. VSV infects both dividing and non-dividing CD34$^+$ cells, and pseudotype vectors expressing VSV envelope proteins are competent to transduce these cells.

Similarly, viral or cellular proteins in general can be co-expressed to increase the host range of an FIV-based vector. Typically, a nucleic acid encoding a selected protein is coexpressed in an FIV packaging cell of the invention. Protein encoded by the nucleic acid is incorporated into the particle which packages an FIV-packageable nucleic acid, which buds off from the packaging cell membrane. If the protein is recognized by a cellular receptor on a target cell, the particle is transduced into the cell by receptor mediated endocytosis. Preferred proteins include viral envelope or coat proteins, cell receptor ligands, antibodies or antibody fragments which bind cell receptors on target cells, and the like.

Preferred Promoters

One class of embodiments utilizes an HIV LTR sequence as a promoter for the FIV packageable vector. These LTR sequences are trans-activated upon infection of a cell containing the LTR promoter by the infecting HIV virus. HIV LTR promoters, in addition to binding tat and rev are responsive to cellular cytokines (such as IL-2 and SP-1) which act to permit transcription of the HIV genome upon infection. Thus, in one embodiment, a therapeutic nucleic acid of choice is placed under the control of an LTR promoter, rendering the cells ordinarily most vulnerable to HIV infection resistant to infection. Furthermore, in one embodiment, an HIV packaging site (in addition to the FIV or other non-primate lentiviral packaging site) is included in the FIV packageable vector. This permits the anti-HIV therapeutic agent encoded in the FIV based vector to be packaged and disseminated by infecting HIV viruses, causing a secondary protective effect to be propagated in combination with HIV infection, thereby slowing the infection. The HIV packaging site is well described, see, Poznansky et al. (1991) *Journal or Virology* 65(1): 532–536; Aldovini and Young (1990) *Journal of Virology* 64(5):1920–1926, and Clever et al. (1995) *Journal of Virology* 69(4): 2101–2109. For a description of vectors which are packaged by HIV to provide a secondary protective effect, see, Wong-Stall et al. U.S. Pat. No. 5,650,309.

Constitutive promoters for directing expression of therapeutic nucleic acids are also preferred, such as pol III promoters. PCT application PCT/US94/05700 (WO 94/26877) and Chatterjee et al. (*Science* (1992), 258: 1485–1488, hereinafter Chatterjee et al. 1) describe antisense inhibition of HIV-1 infectivity in target cells using viral vectors with a constitutive pol III expression cassette expressing anti-TAR RNA. Chatterjee et al. (PCT application PCT/US91/03440 (1991), hereinafter Chatterjee et al. 2) describe viral vectors, including AAV-based vectors which express antisense TAR sequences. Chatterjee and Wong (*Methods, A companion to Methods in Enzymology* (1993), 5: 51–59) further describe viral vectors for the delivery of antisense RNA. PCT publication WO 94/26877 (PCT/US94/05700) describes a variety of anti-HIV therapy genes, and gene therapy strategies generally, including the use of suicide genes, trans-dominant genes, ribozymes, anti-sense genes, and decoy genes in gene therapy vectors. Yu et al. (1994) *Gene Therapy* 1: 13–26 and the references cited therein provides a general guide to gene therapy strategies useful against HIV infection.

Ex Vivo Transformation of Cells

Ex vivo methods for inhibiting viral replication in a cell in an organism (or otherwise introducing a therapeutic gene into the cell) involve transducing the cell ex vivo with a therapeutic nucleic acid of this invention, and introducing the cell into the organism. Target cells include CD4$^+$ cells such as CD4$^+$ T cells or macrophage isolated or cultured from a patient, stem cells, or the like. See, e.g., Freshney et al., supra and the references cited therein for a discussion of how to isolate and culture cells from patients. Alternatively, the cells can be those stored in a cell bank (e.g., a blood bank). In one class of preferred embodiments, the packageable nucleic acid encodes an anti-viral therapeutic agent (e.g., suicide gene, trans-dominant gene, anti-HIV ribozyme, anti-sense gene, or decoy gene) which inhibits the growth or replication of an HIV virus, under the control of an activated or constitutive promoter. The cell transformation vector inhibits viral replication in any of those cells already infected with HIV virus, in addition to conferring a protective effect to cells which are not infected by HIV. In addition, in preferred embodiments, the vector is replicated and packaged into HIV capsids using the HIV replication machinery, thereby causing the anti-HIV therapeutic gene to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides a method of protecting cells in vitro, ex vivo or in vivo, even when the cells are already infected with the virus against which protection is sought.

In one particularly preferred embodiment, stem cells (which are typically not CD4$^+$) are used in ex-vivo procedures for cell transformation and gene therapy. The advantage to using stem cells is that they can be differentiated into other cell types in vitro, or can be introduced into a mammal (such as the donor of the cells) where they will engraft in the bone marrow. Methods for differentiating CD34$^+$ cells in vitro into clinically important immune cell types using cytokines such a GM-CSF, IFN-$\gamma$ and TNF-$\alpha$ are known (see, Inaba et al. (1992) *J. Exp. Med.* 176, 1693–1702, and Szabolcs et al. (1995) 154: 5851–5861). Methods of pseudotyping FIV vectors so that they can transform stem cells are described above. An affinity column isolation procedure can be used to isolate cells which bind to CD34, or to antibodies bound to CD34. See, Ho et al. (1995) Stem Cells 13 (suppl. 3): 100–105. See also, Brenner (1993) *Journal of Hematotherapy* 2: 7–17. In another embodiment, hematopoietic stem cells are isolated from fetal cord blood. Yu et al. (1995) PNAS 92: 699–703 describe a preferred method of transducing CD34$^+$ cells from human fetal cord blood using retroviral vectors. Rather than using stem cells, T cells are also transduced in preferred embodiments in ex vivo procedures. Several techniques are known for isolating T cells. In one method, Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 $\mu$g/ml gentamicin sulfate, 50 $\mu$g/ml streptomycin) supplemented with 1% fetal bovine serum (FBS). Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.).

In general, the expression of surface markers facilitates identification and purification of T cells. Methods of identification and isolation of T cells include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, NY; and Harlow and Lane (1989) *Antibodies: A Laboratory Manual* Cold Spring Harbor Press, NY; Stites et al. (eds.) Basic and Clinical Immunology (4th ed.)

In addition to the ex vivo uses described above, the packaging cell lines of the invention and the HIV packageable nucleic acids of the invention are useful generally in cloning methods. Packageable nucleic acids are packaged in an FIV particle and used to transform an FIV-infectible cell (e.g., a feline hematopoietic cell) in vitro or in vivo. This provides one of skill with a technique and vectors for transforming cells with a nucleic acid of choice, e.g., in drug discovery assays, or as a tool in the study of gene regulation, or as a general cloning vector.

In Vivo Transformation

Non-primate lentiviral particles containing therapeutic nucleic acids can be administered directly to the organism for transduction of cells in vivo. Administration is by any of the routes normally used for introducing a molecule into ultimate contact with blood or tissue cells. Packageable nucleic acids packaged in FIV or other non-primate lentiviral particles are used to treat and prevent virally-mediated diseases such as AIDS in animals and human patients. The packaged nucleic acids are administered in any suitable manner, preferably with pharmaceutically acceptable carriers. Suitable methods of administering such packaged nucleic acids in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

The packaged nucleic acids, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are the preferred methods of administration. The formulations of packaged nucleic acid can be presented in unit-dose or multi-dose sealed containers, such as ampules and vials.

Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of virally-mediated diseases such as AIDS, the physician evaluates circulating plasma levels, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of inhibitor nucleic acid. The vectors of this invention can supplement treatment of virally-mediated conditions by any known conventional therapy, including cytotoxic agents, nucleotide analogues and biologic response modifiers.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

For introduction of transduced cells, prior to infusion, blood samples are obtained and saved for analysis. Between $1 \times 10^8$ and $1 \times 10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis* 6:48–53; Carter et al. (1988) *J. Clin. Arpheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

Viral Inhibitors

Specialized viral inhibitors are typically encoded by the packaged nucleic acids of the invention, where the intended use is viral (e.g., HIV) inhibition. Thus, techniques applicable to the construction and maintenance of nucleic acids apply to the inhibitors of the present invention. Anti-viral agents which are optionally incorporated into the viral inhibitors of the invention include anti-sense genes, ribozymes, decoy genes, and transdominant nucleic acids.

An antisense nucleic acid is a nucleic acid that, upon expression, hybridizes to a particular RNA molecule, to a transcriptional promoter or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to viral gene transcripts. Two target sequences for antisense molecules are the first and second exons of the HIV genes tat and rev. Chatterjee and Wong, supra, and Marcus-Sekura (*Analytical Biochemistry* (1988) 172, 289–285) describe the use of anti-sense genes which block or modify gene expression.

A ribozyme is a catalytic RNA molecule that cleaves other RNA molecules having particular nucleic acid sequences. General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25: 289–317 provides and overview of ribozymes in general, including group I ribozymes, hammerhead ribozymes, hairpin ribozymes, RNAse P, and axhead ribozymes. Ribozymes useful in this invention include those that cleave viral transcripts, particularly HIV gene transcripts. Ojwang et al., *Proc. Nat'l. Acad. Sci., U.S.A.*, 89:10802–06 (1992); Wong-Staal et al. (PCT/US94/05700); Ojwang et al. (1993) *Proc Natl Acad Sci USA* 90:6340–6344; Yamada et al. (1994) *Human Gene Therapy* 1:39–45, Leavitt et al. (1995) *Proc Natl Acad Sci USA* 92:699–703; Leavitt et al. (1994) *Human Gene Therapy* 5:1151–1120; Yamada et al. (1994) *Virology* 205:121–126, and Dropulic et al. (1992) *Journal of Virology* 66(3): 1432–1441 provide an examples of HIV-1 specific hairpin and hammerhead ribozymes.

Briefly, two types of ribozymes that are particularly useful in this invention include the hairpin ribozyme and the hammerhead ribozyme. The hammerhead ribozyme (see, Rossie et al. (1991) *Pharmac. Ther.* 50:245–254; Forster and Symons (1987) *Cell* 48:211–220; Haseloff and Gerlach (1988) *Nature* 328:596–600; Walbot and Bruening (1988) *Nature* 334:196; Haseloff and Gerlach (1988) *Nature* 334:585; and Dropulic et al and Castanotto et al., and the references cited therein, supra) and the hairpin ribozyme (see, e.g., Hampel et al. (1990) *Nucl. Acids Res.* 18:299–304; Hempel et al., (1990) European Patent Publication No. 0 360 257; U.S. Pat. No. 5,254,678, issued Oct. 19, 1993; Wong-Staal et al., PCT/US94/05700; Ojwang et al. (1993) *Proc Natl Acad Sci USA* 90:6340–6344; Yamada et al. (1994) *Human Gene Therapy* 1:39–45; Leavitt et al. (1995) *Proc Natl Acad Sci USA* 92:699–703; Leavitt et al. (1994) *Human Gene Therapy* 5:1151–1120; and Yamada et al. (1994) *Virology* 205:121–126) are catalytic molecules having anti-sense and endoribonucleotidase activity. Intracellular expression of hammerhead ribozymes and a hairpin ribozymes directed against HIV RNA has been shown to confer significant resistance to HIV infection. These ribozymes are constructed to target a portion of the HIV genome, or nucleic acid encoded by the genome. Preferred target sites in HIV-1 include the U5 region, and the polymerase gene. GUC and GUA cleaving trans active anti-HIV ribozymes are known.

A decoy nucleic acid is a nucleic acid having a sequence recognized by a regulatory nucleic acid binding protein (i.e., a transcription factor, cell trafficking factor, etc.). Upon expression, the transcription factor binds to the decoy nucleic acid, rather than to its natural target in the genome. Useful decoy nucleic acid sequences include any sequence to which a viral transcription factor binds. For instance, the TAR sequence, to which the tat protein binds, and the HIV RRE sequence (in particular the SL II sequence), to which the rev proteins binds are suitable sequences to use as decoy nucleic acids.

A transdominant nucleic acid is a nucleic acid which expresses a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. In particular, rev can be made transdominant by eliminating the leucine-rich domain close to the C terminus which is essential for proper normal regulation of transcription. Tat transdominant proteins can be generated by mutations in the RNA binding/nuclear localization domain. Reciprocal complementation of defective HIV molecular clones is described, e.g., in Lori et al. (1992) *Journal of Virology* 66(9) 5553–5560.

EXAMPLES

The following examples are provided by way of illustration only and not by way of limitation. Those of skill will readily recognize a variety of noncritical parameters which are changed or modified to yield essentially similar results.

Example 1

Construction of FIV Packaging Plasmids and Vectors

The FIV long terminal repeat (LTR) is inactive, or minimally active, in human cells. No prior method for high-level expression of the full complement of proteins of a non-primate lentivirus in trans in human cells and in replication-defective fashion has been previously described. Therefore, to express high levels of FIV proteins in trans in replication-defective fashion in human cells, and to enhance safety by replacing a critical portion of FIV needed for replication, FIV clone 34TF10 was cleaved with EspI, treated with Klenow polymerase in the presence of 200 $\mu$M dNTPs, then cleaved with SacI, treated with T4 DNA polymerase in the presence of 200 $\mu$M dNTPs, and the resulting fragment containing the viral coding regions (but not the LTRs) was gel purified. This fragment was then blunt end-ligated into the NotI & XbaI cleaved, Klenow-treated, calf intestinal alkaline phosphatase-treated backbone of the CMV-expression plasmid pRc/CMV. The resulting plasmid (CF1) was confirmed by multiple diagnostic restriction digests. CF1 contains the CMV promoter followed by the FIV genome from the distal portion of the post-LTR 5' leader (93 nt upstream of the major splice donor) to 38 nucleotides downstream of the last ORF (Rev) of FIV.

FIV clone 34TF10 was chosen for this work because this FIV clone already has a mutation inactivating the ORF2 gene. See, Talbott, R. L. et al. (1989) *Proc. Natl. Acad. Sci. USA* 86, 5743–5747. ORF2 is a putative transactivator, which has been shown to be necessary for replication in feline peripheral blood lymphocytes. Thus 34TF10 is an attenuated virus; this attenuation is beneficial for this invention as it further minimizes the risk of wild-type pathogenic FIV while not affecting the vector performance. However, other clones with similar properties are available or can easily be derived by similarly inactivating the wild-type virus using recombinant methods.

Transfection of CF1 into human HeLa, 293 and 293-T kidney cells by the calcium phosphate co-precipitation method produced the surprising result of widespread ballooning syncytia (multi-nucleated giant cells produced by fusion of envelope-expressing cells with other cells) containing fifty to several hundred nuclei and high levels (over one million cpm) of supernatant reverse transcriptase. In fact, we found that human 293 and 293-T cell and HeLa monolayer cultures were reproducibly 90–95% destroyed by syncytia after transient transfection of CF1 (for example by transfection of 10 $\mu$g of CF1 in a 75 cm$^2$ flask), yet as designed and expected, no infectious or replication-competent virus is produced: transfer of large volumes of CF1-transfected 293-T cell supernatant to fresh 293 or 293-T cells or to Crandall feline kidney cells resulted in no syncytia or RT production. CF1$\Delta$env, which is identical to CF1 except for an FIV envelope deletion (see, details below), does not cause syncytia but does produce high levels of reverse transcriptase and of viral functions needed for packaging of vectors. This unprecedented result produced the novel insight that all the functions of FIV needed for protein production, including the Rev/RRE axis of regulation, FIV gag/pol production and envelope-mediated syncytia, can take place in human cells if the FIV promoter is specifically replaced with a promoter active in human cells.

The syncytia produced in human cells by CF1 and CT5 (below) were completely inhibited by inclusion of a 1:1000 dilution of plasma from FIV-infected cats (IC50 between 1:10,000 and 1:30,000 dilution) but were not at all inhibited by any dilution (even 1:10) of plasma from uninfected domestic cats. This specific inhibition by anti-FIV antibody provided further evidence that the syncytia were FIV envelope-specific.

Radioimmunoprecipitation of 35S-methionine and 35S-cysteine-labeled human (293-T, HeLa) and feline (CRFK) cells transfected with CF1 and the parental virus (34TF10) showed that FIV viral proteins could be specifically immunoprecipitated with FIV+sera from CRFK cells transfected with either plasmid. In the human cells, 34TF10 produced little or no protein, indicating minimal activity of the FIV promoter, while CF1 produced large amounts of FIV protein. These proteins were shown to be FIV specific by their absence in immunoprecipitates of the same cells transfected with a control plasmid.

To allow heterologous (e.g., VSV-G) envelope use, specific deletion of the FIV envelope (the product of the env gene) from CF1 was performed by a 3 part ligation: CF1 was restricted with PflMI (which is present 4 times in CF1). Since the two PflM sites of interest in the env gene were incompatible, and because simple blunting of these PflM sites would produce an in-frame env deletion, the PflM digest was treated with T4 polymerase to remove the 3' PflmI overhang and ligated to a frame-shifting sacII linker, digested with SacII, and gel purified. Aliquots of the PflMI/SacII-linked digest were then restricted with sacII and separately with either pvuI or Bsu36I. A 3-part ligation was then performed (PvuI-BsU36I plus BsU36I-PflM(SacII linker) plus (SacII linker)PflMI-PvuI). The resulting plasmid (CF1Δenv), was confirmed by multiple diagnostic restriction digests. CF1Δenv contained an 875 nt deletion in env. It produced high levels of reverse transcriptase in human cells after transfection, but no syncytia, providing further evidence, in addition to the plasma inhibition experiments described above, that the syncytia seen with CF1 were specifically FIV envelope-mediated.

The envelope function for CF1Δenv can be supplied in trans by any number of heterologous viral envelope proteins. These include, but are not limited to, VSV-G, the amphotropic envelope of Moloney murine leukemia virus (MoMuLV), and gibbon ape leukemia virus (GALV) envelope, which are well known to those skilled in the art for being able to efficiently supplant envelope function for retroviruses.

In other embodiments, additional deletions of FIV sequences are made from CF1Δenv. For example, the region between the major 5' splice donor and the gag ATG codon, although only twenty nucleotides in FIV (compared to greater than 40 in HIV-1 and greater than 70 in HIV-2), can be deleted or changed in sequence. Additonal env sequences are removed and tested and the effects of deleting vif or other regions tested.

In a preferred embodiment, it was decided to completely replace the promoter function of the FIV U3 in this system (that is, in both packaging and vector constructs) for several reasons (U3, or 3-prime unique region, contains the promoter/enhancer elements of a retrovirus). First, the FIV LTR is inactive or poorly active in human cells and it was desired to attempt production of a vector in human cells since that could increase the likelihood of subsequent human cell transduction and because good transfection systems using feline cells are not well-characterized. Second, the well-known high levels of expression directed by a promoter such as the hCMV immediate early promoter in defined systems (e.g., the 293T human embryonic kidney cell system) are desirable. Third, replacing U3 in both vector and packaging construct will further help to eliminate the risk of replication-competent FIV. In another modification 80 bases of the 3-prime U3 region was also deleted from the vector, including especially the TATA box. Therefore, replication-competent FIV cannot be regenerated because of this deletion, and because the packaging plasmid has both the env gene deletion and the ORF2-inactivating stop codon. Fourth, having all three components (packaging plasmid, vector, envelope-expression plasmid) driven from the same promoter can enhance synchronized expression and efficient particle formation. Fifth, as described above, human cell production is safer than feline cell production for clinical use because feline cells pose the risk of introducing known or unknown infectious agents into humans.

The design of the construct involves the fusion of the CMV promoter and the FIV genome (from the 5' R repeat on) precisely at the TATA box. First, PCR (synthetic PCRs were performed with exonuclease+Vent polymerase) was performed with a SacI-tailed sense PCR primer homologous to the nucleotides immediately downstream from the FIV TATA box (5'-atataGAGCTCtgtgaaacttcgaggagtctc-3') (SEQ ID NO:4) in combination with an antisense PCR primer (5'-ccaatctcgcccctgtccattcccc-3') (SEQ ID NO:5) homologous to the opposite strand of the FIV gag gene. The PCR product generated was 450 bp. This PCR product was digested with XhoI before sac I digestion (because there is a sac site is immediately following the XhoI site in the FIV LTR and a SacI-SacI fragment would otherwise be generated). After XhoI digestion and subsequent SacI digestion, the 310 bp fragment resulting was (SEQ ID NO:6):

GAGCT/Ctgtgaaacttc gaggagtctctttgttgag-gactttgagttctcccttgagg ctcccacaga tacaa taaata tttga gat-tgaaccctgtc gagtatct gtgtaatcttttttacctgt gaggtctc ggaatcc ggg cc ga gaactt cgcagttggcgcccgaacagggact-tgattgagagtgattgaggaagtgaagctagagcaatagaaagctgttaagcag aactcct g ctgacctaaataggggaagcagta g cagac g ctg ctaacagt-gagtatctctagtgaagc gga C/TCGAGctc.

This fragment was gel-purified away from the 140 bp residue and cloned into the SacI-XhoI backbone of the pRc/CMV plasmid. In summary, this step arranges the FIV LTR sequences downstream of the TATA box in precise register to both the TATA box of the CMV promoter and the replaced TATA box of FIV: it places a SacI site 3 nucleotides downstream of the TATA box just as there is a SacI site 3 nucleotides downstream of the TATA box in the hCMV promoter and it places the FIV R repeat precisely 9 nt downstream from the TATA box just as in the FIV genome. The fusion therefore preserves (and conjoins) the nucleotide spacing of both the CMV promoter and the FIV transcriptional sequences and is detailed in the sequence below:
acgtataagttgttccattgtaagagtaTATAAccagtgctt tgtgaaacttcgaggagtctctttgttgagga FIV (SEQ ID NO:7);
AGGCGTGTACGGTGGGAGGTCTATATAAGCAGAG-CTCTCTGGCTAACTAGAGAACC . . . pRc/CMV (SEQ ID NO:8);
AGGCGTGTACGGTGGGAGGTC-TATATAAGCAGAGCTCtgtgaacttcgaggagtctctttgttgagga CRFI (SEQ ID NO:9).

CRFI completed the 5-prime fusion of the CMV promoter to the FIV R repeat, but the 3-prime LTR and the remainder of the FIV genome remained to be placed downstream. Therefore, sal I-tailed PCR primers F3'S (tatataGTCgactagggactgtttacgaac) (SEQ ID NO:10) and F3' A/Not (atatatagtcgacGCGGCCGCtgcgaagttctcg) (SEQ ID NO:11) were used to amplify the 3' FIV LTR: the SaLI-digested PCR product was ligated into the alkaline phosphatase-treated compatible Xho I site of CRFI and the ligation was heat-inactivated and selected against wild-type with Xho I. The resulting plasmid, named CRF(L), has both LTRs, and places a unique NotI site at the 3' terminus of the 3' LTR.

Next, the major coding region of the FIV genome was inserted by ligating the 8,845 nt BbeI-EspI fragment of p34TF10 into the phosphatased BbeI-EspI backbone of CRF(L). The resulting plasmid was called CT5 (for CMV promoter→fusion at Tata Box→complete FIV genome from R repeat to normal proviral terminus at the 3' LTR U5 element). CT5 encodes full-length, infectious FIV which is promoted from the CMV promoter in the first round (subsequent rounds is FIV LTR promoted since reverse transcription generates a wild-type U3 at the 5' provirus terminus). Transfection of either CT5 or the wild-type 34TF10 in human 293-T cells resulted in both equivalent levels of RT in supernatants and in widespread syncytia in a standard assay for FIV replication: syncytia formation on 0.5% serum-maintained feline Crandall feline kidney cells (CRFK cells) following transfer of filtered supernatant from the transfected 293-T cells (See also, Tozzini et al. (1992) *Journal of Virological Methods* 37, 241–252). However, identically to 34TF10-generated virus, CT5-generated virus is fully wild-type in its tropism: it does not replicate in human cells. This is expected since the three-prime U3 of CT5 is wild type (retroviruses carry their promoter at the three-prime end of the virion mRNA: reverse transcription results in placement of a copy of the three-prime U3 at the 5' end of the integrated provirus where it acquires the ability to promote subsequent rounds of transcription in susceptible cells). In summary, FIV that is replication-competent for feline cells was produced by transfection of CT5 into adherent cell lines, including 293T cells, proving that the productive phase of the life cycle, but not replication, was efficiently achieved in human cells.

FIV Vectors Derived from CT5

Whether transfected into human or feline cells, CT5 generates FIV that is replication-competent for feline but not human cells: the viral transcripts are expressed from a human, not feline, promoter in producer cells, but the feline three-prime U3 remains intact and the source of the five-prime U3 promoter in any subsequent round of replication is always the three-prime U3 of the producer cell transcript. This remaining three-prime U3 element can also be deleted.

To generate retroviral vectors from modifications of CT5, two strategies were used. One embodiment takes note of the fact that the RRE of FIV is located three-prime to coding sequences in FIV (at the end of the TM protein rather than at the SU/TM junction as in other lentiviruses). Therefore, if a reporter gene cassette having its own polyadenylation p(A) signal is placed in antisense orientation with respect to the FIV sequences, the position of the RRE will be preserved enhancing utilization of cis-acting signals and packaging. In a second embodiment, the RRE was removed from its usual 3-prime location and placed by standard cloning techniques immediately after a portion of the FIV gag/pol gene allowing both Rev protection of the gag sequence-containing vector transcript and insertion of a reporter gene cassette in sense orientation downstream. The gag gene sequences are included in these vectors because they have been shown to enhance packaging in other retroviruses. However, in these vectors, the gag gene is frameshifted by blunted closure of a Tth III 1 site located at nucleotide 298 of gag (cloned by Tth III1 digestion, Klenow polymerase-mediated filling, ligation, ligase inactivation, and finally Tth III 1 selection against wild type) to prevent recombination of functional gag and to prevent generation of a transdominantly-supressive Gag protein. Additional portions of gag beyond or even preceding this frameshift can be removed from vectors without affecting titer.

Note that transcription of these vectors occurs from the CMV promoter and not the FIV promoter. Other promoters are optionally employed. In addition, multiple modifications are possible by deleting additonal regions of the FIV genome, e.g., regions of gag, as detailed below.

Such vectors are described and illustrated below:

1. Vector CTAGCgfsB. The underlined, bold-faced letters in the capsule descriptions, such as the one in parentheses here, indicate the derivation of the name of the vector (CMV promoter joined at TTA box driving expression of an internal reporter gene cassette CMV-GFP-p(A) in reverse orientation and having a gag gene frame shift mutation and subsequent insertion of the sv40T antigen binding site to cause plasmid amplification after transfection in SV40 T antigen-expressing cells). CTAGCgfsB was constructed by three-part ligation of the pvuI-EcoR1 fragment of CT5, the EcoR1-Spe1 fragment of a green fluorescent protein (GFP) gene-containing plasmid, pZcmvGFPpA, and the SpeI-PvuI fragment of CT5. This ligation places the CMV promoter-GFP-p(A) signal cassette in reverse orientation between EcoRI and SpeI in the FIV genome. Next, the Tth III 1 site in the portion of gag/pol remaining in the vector was cleaved, filled in with Klenow polymerase in the presence of 200 μM dNTPs and closed with T4 DNA ligase. This blunting inserts an extra G residue which frameshifts the gag fragment within a few bases of the Tth III 1 site. No pol sequences are present. Therefore, the gag/pol precursor must be supplied in trans from CF1Δenv or subsequent modifications of CF1Δenv. Moreover, this step reduces the chance of wild-type recombination and the chance that a transdominantly-interfering Gag protein fragment will be produced. Finally the sv40-promoter-neoR cassette from pRc/CMV was inserted in the plasmid outside of vector sequences in order to benefit from Sv40 T antigen-driven plasmid amplification and to allow selection for neoR if needed. In one modification, the gag gene ATG start codon can be mutagenized to a stop codon. Also the region between the BsRG1 site and upstream PstI sites is optionally deleted to remove more of gag.

2. Vector CTRZLb. (CMV promoter joined at TATA box driving expression beginning with the R repeat of an internal sense-oriented LacZ reporter gene cassette and having the 3' LTR after lacZ; It also has a gag gene frame shift mutation at the Tth III 1 site and subsequent insertion of the sv40 T antigen binding site to cause plasmid amplification after transfection). To construct this vector, CTAGCgfs was deleted between EcoR1 and BsrG1 by cleavage with these enzymes, Klenow treated with 200 μM dNTPs, blunted closure ligated with T4 ligase and selected against wild-type with EcoR1. The BsrG1 site was regenerated. The BsrgI-EcoNI fragment of pz-lacz was Klenowed and blunted into the unique EcoNI site. The structure was thus: CMV promoter—Tata box fusion with FIV R repeat—U5—Δgag—FIV Rev Response element—cmv promoter-LacZ gene—LTR. Finally, the sv40-promoter-neoR region from pRc/CMV was inserted in the plasmid downstream of the vector to provide a T Antigen binding site in order to benefit from Sv40 T antigen-driven plasmid amplification and to allow selection for neoR if needed. The gag gene ATG start codon can be mutagenized to a stop codon and additional portions of gag are optionally deleted.

Vector supernatants generated by the calcium phosphate co-transfection method were titered on human (HeLa, 293) and feline (CRFK, Fc3Tg) cells. Compared to conventional Moloney murine leukemia virus (Mo-MuLV)-based retroviral vectors the FIV vectors were equally efficient at transducing human and feline cells. Titers of $10^7$ were achieved on both feline and human cells after a single round of concentration by ultracentrifugation. Higher titers are achievable with refinement of transfection and further ultracentrifugation. In addition, both Human (HeLa) and feline (CRFK) cells are efficiently transduced when growth-arrested using aphidicolin 15 μg/ml in the culture medium added 24 hours prior to transduction and replaced daily through lacZ staining. LacZ titers with the FIV vector in aphidicolin-arrested cells were 80–90% of those in dividing cells, while Mo-MuLV vectors transduction was eliminated by aphidicolin treatment. These results indicate that the FIV vector can transduce human cells and clearly has lentivirus-specific biological properties lacking in conventional (e.g., murine) retroviral vectors: the ability to transduce non-dividing cells. Importantly, we detected no preference of the FIV vectors for feline cells: the relative transduction of various human and feline cells was cell-specific not vector-specific. In other words, cells for which transduction by the FIV vector were efficient were also efficiently transduced by conventional Moloney murine leukemia virus vectors, and vice versa.

This invention is applicable to human gene therapy. As detailed above, these retroviral vectors have safety advantages over HIV-based lentiviral vectors because HIV vectors are derived from lethal human pathogens. Since FIV vectors can be worked with in BL-2 level facilities, risks posed to personnel involved in their production are lessened compared to HIV vectors, and ease and convenience of production is enhanced. These vectors have advantages over other gene delivery methods if stable gene transfer to non-dividing or infrequently dividing cells is desired. Such cells include, but are not limited to, cells of the human nervous system, eye, hematopoietic system, integument, endocrine system, hepatobiliary system, gastrointestinal tract, genitourinary tract, bone, muscle, cardiovascular system and respiratory system. These vectors also prevent exposure of patients to non-human cells and prevent exposure to lentiviral genes or lentiviral proteins derived from known pathogens.

Example 2

FIV Based Lentiviral Vector Transduction of Non-Dividing Human Cells and Demonstration of a CXCR4 Requirement for FIV Infection and Cytopathicity HIV-based lentiviral vectors efficiently transduce non-dividing cells, but are problematic because of their derivation from lethal human pathogens. However, use of the non-primate lentiviruses was complicated by a relative lack of knowledge about their molecular properties, particularly their adaptability to human cells. This example describes both productive and post-receptor infective mechanisms of the FIV life cycle in human cells and shows that the functions necessary for lentiviral vector transduction can occur at high efficiency. Substitution of the FIV promoter, which functioned poorly in non-feline cells was performed. An entirely heterologously-promoted and env-pseudotyped FIV vector system demonstrated high level human cell expression and processing of FIV proteins in trans and produced FIV retroviral vectors that transduced dividing, growth-arrested and post-mitotic human cells (macrophages and hNT neurons) at high titer. The system eliminates safety risks of feline producer cells. Severe cytopathicity of heterologously promoted FIV envelope protein in human cells was observed and vectors of the invention were used to investigate this phenomenon. Expression of the FIV genome from the human cytomegalovirus promoter induced profuse, Env-specific syncytia in a wide variety of human cells but not in rodent cells. Moreover, this fusogenic activity required co-expression of CXCR4, the co-receptor for syncytium-inducing strains of HIV. However, despite its CXCR4-dependence, non-host cell FIV Env syncytium induction was dissociable from viral entry: CXCR4 expression in non-feline cells permitted FIV Env-specific cell fusion but neither FIV Env-mediated vector transduction nor viral replication. Consistent with a co-receptor role, human CXCR4 expression in feline cells changed viral phenotype from non-cytopathic to highly cytopathic and increased both viral infectivity and transduction by FIV-enveloped vectors. Utilization of CXCR4 by evolutionarily distant lentiviruses implicates a fundamental role for this chemokine receptor in lentiviral replication and cytopathicity. The results have implications for comparative lentivirus biology as well as for human gene therapy.

An ORF2-defective molecular clone (FIV 34TF10)19 of the Petaluma strain was used (FIG. 1). At the top of FIG. 1, FIV 34TF10 and plasmid CF1 are shown. Further modifications of CF1 used in this study are illustrated and described under the drawing for FIV 34TF10. To generate CF1, the Sac1-Esp1 fragment of 34TF10 was blunt-end ligated between Not1 and Xba1 in the polylinker of the hCMVIE promoter expression plasmid pRc/CMV (Invitrogen). Fusion of hCMVIE promoter to FIV genome between TATA box (CMVIEp-derived) and start of R repeat (FIV-derived) was performed and is shown for plasmid CT5 (junction at the Sac1 site). The PCR-generated fusion arranges the FIV R repeat sequences downstream of the CMV TATA box in precise register to the replaced FIV TATA box; it also drives exression of the vectors (bottom), which lack all vif, ORF2, pol and env sequences. The marker gene cassette is in sense orientation for lacZ and antisense orientation, with an additional poly(A) signal, for GFP. A frameshift was introduced in the vectors at nt 298 of the remaining gag fragment. To generate pseudotyped vector, the VSV-G expression plasmid pHCMV-G 42 (not illustrated) was co-transfected in 293T cells with CF1Δenv and the vectors shown. Additional cloning details are found in Example 1.

34TF10 productively infects Crandell feline kidney cells (CRFK cells) but not feline peripheral blood lymphocytes or primary feline macrophages (Carpenter & O'Brien (1995) Current Opinion in Genetics and Development 5, 739–745; Waters et al. (1996) Virology 215, 10–16; Sparger et al. (1994) Virology 205, 546–553; Bandecchi et al. (1995) New Microbiologica 18, 241–252; Tozzini et al. (1992) Journal of Virological Methods 37, 241–252 (1992); Olmsted et al. (1989) Proceedings of the National Academy of Sciences of the United States of America 86, 2448–2452). This restricted tropism maps to the ORF2 mutation, not env: repair of ORF2, a putative LTR transactivator, results in productive 34TF10 infection of all of these feline cell types36. The 34TF10 envelope may thus be considered by loose analogy to HIV to be "dual-tropic;" however, the lab adapted/T-tropic versus primary/Macrophage-tropic classification has not been established for FIV strains or clones. In fact, although CD4-depletion leading to AIDS is characteristic, FIV also infects CD8+ T cells and B cells as well as CD4+ T cells in infected felines (Pedersen (1993) supra). Neither 34TF10 nor any other domestic cat strains or clones are cytolytic in CRFK cells; small multi-nucleated giant cells (4–12 nuclei) can be detected in a maximally infected culture, but extensive cell death does not occur (Barr et al. (1995), supra; Tozzini et al. (1992) Journal of Virological Methods 37, 241–252; Barr (1997) Virology 228, 84–91). 34TF10 does not cause significant viremia or disease in experimentally infected domestic cats; the in vivo phenotype of the ORF2-repaired clone is not yet known (Sparger et al. (1994) Virology 205, 546–553).

As diagrammed in FIG. 1, the human cytomegalovirus immediate early gene promoter (hCMVIEp) was arranged either (a) to replace all of the FIV LTR with a junction 97 nt upstream of the FIV major 5' splice donor (in plasmid CF1) or (b) to selectively replace the FIV U3 promoter elements (in plasmid CT5, and in FIV vectors) through a fusion at position −14 between the TATA box and the start of transcription, i.e., the R repeat. The arrangement places the CMV TATA box in precise register to the replaced FIV TATA box with respect to the start of transcription (position −27). CF1 lacks both LTRs except for the 89 nt portion of the three-prime U3 that overlaps the rev ORF (FIV has no homologue to HIV nef), thus deleting cis-acting sequences needed for replication and integration (U3 promoter sequences, tRNA primer binding site, R repeats, U5 elements). See also, Example 1 for details of the cloning of the constructs described in this example. CF1Δenv has an additional 875 nt deletion in env which spans the SU-TM junction and is also frameshifting: this plasmid, which was used for packaging of pseudotyped vectors, is thus defective for ORF-2, env, and the cis-acting retroviral elements noted. CT5, in contrast, encodes fully wild-type, replication-competent 34TF10. The system therefore eliminates the need for the feline promoter. The function of ORF2 is not conclusively defined, but FIV LTR-transactivating activity described forits gene product36 would thus also be dispensable.

Transfection of CF1 or CT5 but not 34TF10 into human cells resulted in explosive syncytium formation within 12–18 hours. HeLa cell and 293 human embryonic kidney cell monolayers were reproducibly 90–95% destroyed by syncytial lysis within 48–60 hours after transfection of CF1 or CT5 (FIG. 1). All three plasmids always produced many fewer (400 fold), smaller (4–12 nuclei) syncytia and no discernible cytolysis in CRFK cells.

Transfections were by calcium phopshate preicpitation except for U87MG and U87MG.CXCR4 cells, which were electroporated. In all cases, transfected cells in this study were compared by quantitative syncytial focus assay using cells simultaneously transfected with the same calcium-phosphate precipitate. Cells were stained by crystal violet or, for focal infectivity assays, by immunoperoxidase staining with FIV-Petaluma sera and a secondary horseradish peroxidase-conjugated goat antibody to feline IgG41. All comparisons were controlled by co-transfection of an hCMVIE-promoted GFP or LacZ reporter plasmid as 10% of the input DNA; only experiments with transfection efficiencies varying <5% between compared cell lines are reported. Where lysis was extensive at 24 hours for CF1, comparative transfection efficiency by GFP fluorescence was assayed in parallel wells in the presence of a 1:300 dilution of FIV-infected domestic cat plasma to inhibit syncytium formation. All cells were ATCC lines propagated in 10% bovine serum with antibiotics; CRFK cells were grown in L50 medium as described. The ATCC no for CRFK is ATCCCCL94.

Consistent with previous studies (Barr et al. (1995) *Journal of Virology* 69, 7371–7374) 34TF10 and CT5 transfection of CRFK cells (ATCC CCL 94) established persistent infection with high levels of RT (>5×10$^5$ cpm/ml) by day 7–14, but minimal cytopathic effect (6–12 +/–4 syncytia, 4–8 nuclei each, per 9.6 cm$^2$ well of a six well plate). However, as expected CF1 did not produce infectious virus: passage of filtered supernatant from CF1-transfected human or feline cells to 10$^7$ CRFK cells or to 10$^7$ human cells (HeLa, 293, H9, Molt4, supT1, U937) produced no syncytia or RT production; the adherent cell lines were also negative by a previously described focal infectivity assay (FIA) (Remington et al. (1991) *Journal of Virology* 65, 308–312), sensitive to <5 infectious units per ml in 34TF10- or CT5-infected CRFK cells.

Whether produced in human or CRFK cells, neither p34TF10- nor CT5-generated FIV replicated in any human cells. Nevertheless, the syncytia produced by CF1 and CT5 transfection into human and feline cells were specifically caused by the FIV envelope protein, since transfection of CF1Δenv never produced syncytia in any cells, but did yield comparably high levels of RT.

Mg2$^+$ dependent reverse transcriptase was measured as described previously (Willey et al. (1988) *Journal of Virology* 62, 139–147) 52 hours after transfection of indicated plasmids in CRFK cells, HeLa, 293 and 293T cells. Extensive syncytial lysis was seen in cells transfected with CT5, CF1, CF1Δpol and pHCMV-G. The latter two plasmids were included as controls for cell lysis to verify viral specificity. Supernatant from H9 cells infected 2 weeks earlier with HIV-1 and HIV-2 at m.o.i of 1.0 were also assayed for comparison. In FIG. 2, each point is the mean of triplicate measurements±S.E. Radioimmunoprecipitation of transfected cells with FIV (Petaluma strain)-infected domestic cat plasma was performed. 293 cells, HeLa and CRFK cells were transfected with the indicated plasmids by calcium phosphate precipitation in 25 cm$^2$ flasks. At 27 hours (293 cells) or 48 hours (HeLa and CRFK cells) after transfection, cells were radiolabeled for five hours with $^{35}$S-cysteine and $^{35}$S-methionine in cysteine- and methionine-free medium with 7.5% dialyzed fetal bovine serum after a one hour pre-incubation in this medium without isotope. Lysates were pre-cleared with normal cat serum and protein A sepharose, incubated overnight with 10 μof FIV-infected cat plasma, precipitated with protein A separose, and electrophoresed with pre-stained markers in 10 or 12.5% SDS polyacrylamide gels. Lysates were derived from approximately 15–25% the amount of cells in the other lanes because of loss of cells to extensive syncytial lysis. Panel B shows inhibition of CF1-induced syncytia in 293T and HeLa cells by FIV-infected domestic cat plasma. Syncytia were scored at 48 hours as foci with ≧8 nuclei by crystal violet staining of methanol-fixed cells. Dilutions of either FIV+(squares, circles) or FIV−(diamonds, triangles) plasma were added to cells at the time of transfection in 12 well plates and again with change of medium 14 hours later.

Figure 2A:
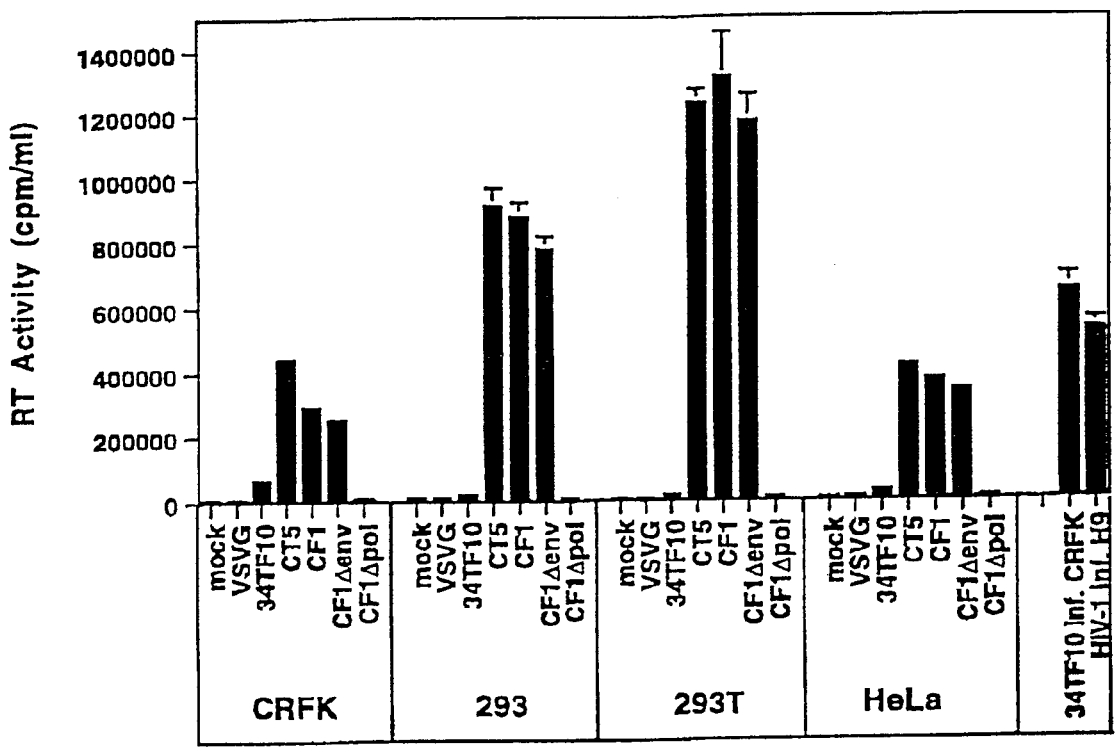
FIG. 2 panels A and B provide experimental results is graphic form.
Figure 2B:
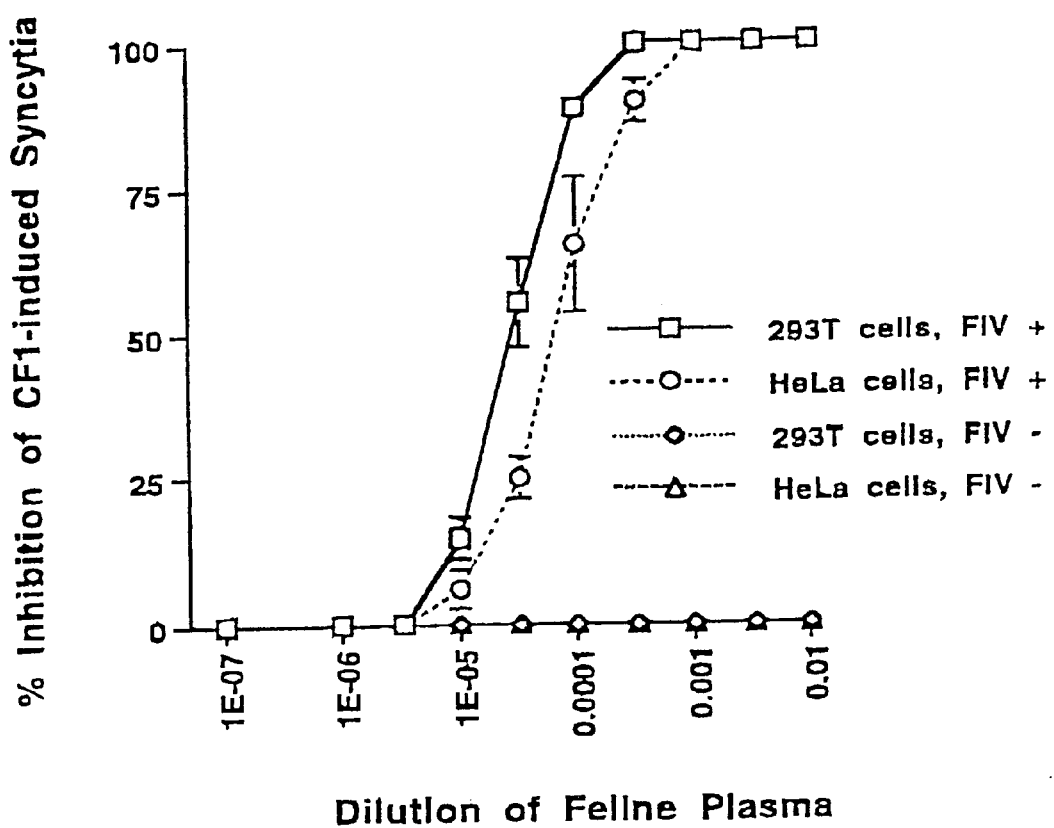

Syncytia in CF1-transfected human cells were potently suppressed by FIV Petamula strain-infected domestic cat plasma with 50% inhibition on 293T and HeLa cells at 1:32,000-fold and 1:12,700-fold dilution respectively, while pre-immune domestic cat plasma had no effect on syncytium formation at any dilution, even 1:10 (FIG. 2B). Moreover, syncytium induction was abrogated by a smaller, 539 nt (nt 7322–7861), non-frameshifting deletion confined to the SU portion of env (sparing the TM domain and the upstream proteolytic cleavage site; see CF1ΔSU in FIG. 1) suggesting that both the SU and TM domains of the envelope are required for syncytium-induction. Transfection efficiencies determined by GFP reporter co-transfection in parallel wells in the presence of 1:300 diluted antiserum for the experiments were ≦10%, showing that syncytial lysis was mediated by fusion of non-transfected cells with transfected cells.

Expression in human cells was then further examined by reverse transcriptase (RT) assays and by immunoprecipitation of radiolabeled cells with plasma from FIV-infected domestic cats. hCMVIE-promoted constructs expressed high levels of Mg2$^+$-dependent RT in human cells (HeLa, 293, 293T), and were also superior to the native LTR of p34TF10 in both feline (CRFK) cells and human cells (FIG. 2A). In contrast, LTR-directed RT expression by 34TF10 in human cells was minimal; protein expression by the hCMVIEp-chimeric constructs also exceeded 34TF10 expression in the feline cells by a factor of approximately six-fold. A pol- deletion mutant (CF1Δpol) produced no RT (FIG. 2A) but produced syncytia as extensively as CF1.

Immunoprecipitation of transfected, radiolabeled human and feline cells demonstrated a wild-type 34TF10 pattern of expression by CF1 or CT5 in human cells in amounts commensurate with the RT assays. p34TF10 expression was nevertheless clearly detectable by RIPA in HeLa cells, but at considerably lower levels than the CMVIEp-chimerics, and was undetectable (even after prolonged film exposure) in 293 or 293T cells. Consistent with this result, small syncytia (4–6 nuclei, 11–14 syncytia±4, n=4, per well of a six well plate) were detectable in HeLa cells 48 hours after p34TF10 transfection. The frame-preserving SU deletion of CF1ΔSU resulted in the predicted truncated envelope precursor; it runs in a poorly resolved smear with the shortened SU/gp100 cleavage product. The plasma used did not precipitate the TM protein from any cells. The other two env mutants abrogated immunoprecipitable Env production and no envelope mutant formed syncytia in any cells. Consistent with the RT data, CF1 expression was also superior to LTR-driven expression in CRFK cells.

Taken together, these data show that high level expression of the full genomic repertoire of a non-primate lentivirus occurs in human cells and that promoter substitution permits the productive phase of FIV replication (including the Rev/RRE regulatory axis, splicing, production of both Gag/Pol and Env precursors, and correct proteolytic processing of each) to occur with maximal efficiency in human cells and at higher levels than seen with either the native promoter or the CMVIE promoter in CRFK cells. Selective U3 replacement (in CT5 and for use in vectors described below) and full LTR substitution (for protein production in trans) were both effective.

To examine post-entry phases of the FIV life cycle in human cells, CT5 was used as the starting point for constructing retroviral vectors containing internally promoted marker gene cassettes that replace pol, env and the accessory genes as well as a portion of gag. A frameshift mutation was introduced in all vectors at nt 298 of the remaining gag ORF by blunted closure of a TthIII 1 site, generating a stop codon at nt 319 (FIG. 1). Vector CTRZLb was co-transfected with CF1Δenv and the VSV-G expression plasmid pHCMV-G in 293T cells by calcium phosphate co-precipitation. At 48–96 hours after transfection, supernatants of the FIV vector and of a control VSV-G-pseudotyped Mu-MLV lacZ vector were cleared, filtered (0.45 $\mu$M), titered on HeLa cells and then re-titered by limiting dilution on a panel of feline and human cell lines; the experiments were done with cells that were either growing or arrested in G1/S with aphidicolin at 20 $\mu$g/ml. High titers ($10^6$) equivalent to those of a conventional Moloney murine leukemia virus retroviral vector were achievable with a single round of concentration (Burns et al. (1993) *Proceedings of the National Academy of Sciences of the United States of America* 90, 8033–8037) by ultracentrifugation. Similar to HIV vectors, the FIV vector was minimally affected by cell cycle arrest, while the Mu-MLV vector transduction was eliminated, thus demonstrating this lentivirus-specific property of the FIV vector and transferablity of this property to human cells. Equally importantly, when compared in growing cells to the VSV-G psudotyped Moloney murine leukemia virus lacZ vector, the FIV vector displayed no significant preference for feline cells (compare titer ratios, see plot in Table inset). When allowed to proliferate after transduction with CTRZLb, large (100–400 cells) homogeneously lacZ-positive colonies were generated, indicating stable, clonal maintenance of the transgene. Although cell lines varied considerably in transducibility as expected, these differences were equivalent for the Moloney and FIV vectors: that is, they were cell-specific rather than vector specific and reflects susceptibility to VSV-G-mediated transduction. The chief block to the infective stage of the FIV life cycle in non-feline cells is thus shown to be at the level of virion entry rather than further downstream.

To further assess the ability of the FIV vectors to transduce non-dividing human cells, we transduced post-mitotic human cells, employing the two most developed, definitive human tissue culture models: primary human macrophages and hNT neurons. hNT neurons are irreversibly differentiated, polarized human neurons derived from the NT2 teratocarcinoma cells by a six week process employing retinoic acid and several mitotic inhibitors. Third-replate hNT cells, employed here, are irreversibly post-mitotic, remaining so a year after transplantation into the brains of nude mice, morphologically resemble primary neurons, express a plethora of neuron-specific markers, and grows clumps of neurons that elaborate functional axons and dendrites. hNT neurons transduced at an moi of 1.0. showed lacZ staining was visible both in cell bodies and in processes. Primary human macrophages showed high background lacZ staining and were therefore transduced with GFP vector CTAGCb on day nine after isolation from peripheral blood of normal donors. These cells were transduced at high titer by the FIV vector but not by a GFP-transducing Mu-MLV vector.

The determinants of FIV encapsidation have received no previous study. Lentiviral encapsidation signals are more complex than those of the murine oncovirinae (Lever, (1996) *Gene Therapy* 3, 470–471). The LTRs were deleted from CF1Δenv to prevent packaging and remove sequences needed for reverse transcription and integration; the 20 nucleotides between the major splice donor and the gag gene, a putative contribution to lentiviral packaging, is exceptionally short in FIV (20 nt compared to 44 nt in HIV-1, 75 nt in HIV-2 and 375 nt in Mu-MLV). Scrambling and deletion of this region may improve titer.

To test whether FIV structural gene-encoding sequences were transferred to target cells by transduction with CF1-packaged vector, $10^6$ CRFK cells were transduced at m.o.i.= 10 with DNAsed CTRZLb vector, yielding 99% transduction. 1 $\mu$g of genomic DNA from these cells was negative by PCR for gag sequences, while simultaneous amplification of the same amount of this DNA spiked with genomic DNA from as few as 10 cells from a chronically 34TF10-infected CRFK culture was positive.

Severe cytopathicity that resulted when FIV envelope expression was enabled in human cells. Because of the recent discovery of CXCR4 as the co-receptor for syncytium-inducing strains of HIV, these observations raised immediate questions of specific mechanism. The FIV primary receptor remains unknown. Since most human cell lines, including HeLa and 293 cells, express appreciable levels of CXCR4, we next employed those rare human lines known to express no CXCR4 (U87MG and SK-N-MC cells) or extremely low levels of CXCR4 (HOS cells) Berson et al. (1996) *Journal of Virology* 70, 6288–6295; Endres et al. (1996) *Cell* 87, 745–756; Harouse & Gonzalez-Scarano (1996) *Journal of Virology* 70, 7290–7294). Transfection of CF1 or CT5 into U87MG and SK-N-MC cells (by electroporation or calcium phosphate co-precipitation) never resulted in syncytium formation (n=9 for each line, transfection efficiencies≧10% by GFP reporter co-transfection). In addition, while CF1-transfected rat 208F cells readily fused with a variety of human cell lines and with CRFK cells, fusion did not occur with SK-N-MC or U87MG cells. In addition, transfection of other rodent cells (NIH 3T3, CHO) cells did not produce syncytia (n=8, efficiencies≧10% by GFP co-transfection).

We therefore constructed an MMLV-based retroviral vector, pZ.CXCR4, that expresses human CXCR4 and neoR from a bicistronic mRNA and used it to generate a panel of G418-selected U87MG, HOS, SK-N-MC, NIH3T3 and CRFK cell lines expressing human CXCR4. Control G418-selected lines were generated with the parental retroviral vector, pJZ30854. Expression of CXCR4 was documented in all pZ.CXCR4-transduced lines. Transfection of CF1 or CT5 into U87MG.CXCR4, SK-N-MC.CXCR4, 3T3.CXCR4, but not simultaneous transfection into the respective control lines (n=8 for CF1, n=6 for CT5), produced exuberant syncytia. Moreover, while small 4–8 cell syncytia could be consistently observed in CF1-transfected HOS cells, CF1-transfected HOS.CXCR4 cells produced massive multinucleated giant cells containing several hundred nuclei. To confirm these results, we also carried out feline/human cell mixing studies with 3201-FIV cells (chronically FIV-infected feline cat lymphoma cells, ATCC CRL 10909). U87MG, SK-N-MC, HOS, 3T3 cells, their respective pZ.CXCR4 vector-selected counterpart lines, and HeLa cells, were each plated ($3\times10^5$ cells) in six well plates. $10^5$ 3201-FIV cells per well were added the next day. At 18 hours, large ballooning syncytia (involving 30–80% of the monolayer) of the HeLa cells and each CXCR4-expressing line were observed; no syncytia at all were seen at any time point in U87MG, SK-N-MC, HOS, or 3T3 cells.

Transduction by FIV Env was then examined using co-transfection of CF1 and CTRZLb in 293T cells. As shown in Table 1, this vector was unable to transduce any human lines, regardless of CXCR4 expression; transduction could be detected in CRFK cells, but at very low titer (<10 transducing units/ml). CRFK CXCR4 cells, in contrast, were transducible at least 2 logs higher titer ($3.6\times10^2$) than CRFK. Moreover, the ligand for CXCR4 inhibited vector transduction via FIV envelope.

Since the vector data indicated that CXCR4 increased feline cell viral entry as well as more broadly mediating fusogenesis, we next compared the infectivity of replication-competent FIV on CRFK cells and CRFK.CXCR4 cells. Each line was seeded into 48 well plates at $10^4$ cells per well and infected the next day with serial four-fold dilutions of a 34TF10 virus stock produced in CRFK cells. To reduce artifactual loss of titer from the marked cytopathicity of 34TF10 in CRFK.CXCR4 cells, the plates were fixed and examined at 40 hours after infection by a focal infectivity assay (employing 1:500 dilution of the FIV-positive sera and a secondary horseradish peroxidase-conjugated anti-feline IgG antibody) sensitive to 1 in $10^6$ infected cells (see also, Remington et al. (1991) *Journal of Virology* 65, 308–312 and Chesebro & Wehrly (1988) *Journal of Virology* 62, 3779–3788). 34TF10 was eight fold more infectious on CRFK.CXCR4 than on CRFK (p=0.0002). We consider this a minimum estimate of infectivity ratio, since numerous rounded floating or poorly adherent cells that stained by IFA were present in the infected CRFK.CXCR4 wells as early as 40 hours (but not in uninfected control wells or infected CRFK wells) and were not counted. To confirm these results, limiting dilution titration of 34TF10 on the two cell lines was carried out by infecting as above; cells were split at four-five day intervals for three weeks and positive wells were identified by RT assay.

Taken together these results show that fusogenic activity and viral entry of distantly related primate and non-primate lentiviruses are mediated by the same cell surface molecule. This broad utilization of CXCR4, for a non-primate lentivirus that does not utilize CD4 as a primary receptor, implicates a fundamental role for CXCR4 in lentiviral syncytiagenesis and in AIDS pathogenesis. Our experiments do not exclude that low-level FIV envelope-mediated infection of human cells occurs, perhaps via CXCR4 alone, as has been well-described for some isolates of HIV-1 and HIV-2 (Endres et al. (1996) *Cell* 87, 745–756; Harouse & Gonzalez-Scarano (1996) *Journal of Virology* 70, 7290–7294; McKnight et al. (1994) *Virology* 201, 8–18; Reeves et al. (1997) *Virology* 231, 130–134; Potempa et al. (1997) *Journal of Virology* 71, 4419–4424; Harouse et al. (1995) *Journal of Virology* 69, 7383–7390; Talbot et al. (1995) *Journal of Virology* 69, 3399–3406; Tateno et al. (1989) *Proceedings of the National Academy of Sciences of the United States of America* 86, 4287–4290 (1989). Clapham et al. (1992) *Journal of Virology* 66, 3531–3537) but indicate that, as in most of these examples, such a process is inefficient. Similarly, rabbits can also be infected by HIV-1, but the process is quite inefficient (Gardner & Luciw (1989) *Faseb Journal* 3, 2593–2606). Our data are consistent with the existence of a primary FIV receptor. In addition to the vector data, for example, HeLa cells do not support productive FIV replication but were easily transducible with the VSV-G pseudotypes, expressed abundant CXCR4, exhibited extensive Env-specific cytopathicity, showed low but significant levels of FIV LTR-directed expression, permitted normal viral protein processing, and generated replication-competent FIV from plasmid CT5.

The results therefore have important implications for lentivirus biology and for human gene therapy. By showing that a non-primate lentivirus also utilizes CXCR-4 for both cell fusion and viral entry, our data show that this chemokine receptor plays a broadly fundamental role in lentivirus replication, in syncytiagenesis, and perhaps in pathogenesis. It is also likely that in vivo replication of FIV has additional and more subtle requirements. FIV vectors therefore represent an inherently safer alternative to HIV vectors. Epidemiologic support for this hypothesis is strongest for FIV than for any other non-primate lentivirus, because FIV has shown no ability to infect or cause disease in humans after natural inoculation in many humans over many years by the same principal infective route operative in cats (cat bites). Furthermore, in addition to U3, ORF2 and env, additional deletions of FIV sequences from both vectors and packaging plasmids are possible. FIV vectors are logistically easier to produce since infectious FIV is routinely propagated in Biosafety Level 2 tissue culture (vectors herein are approved for BL-2 use by the UC San Diego Institutional Biosafety Committee).

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A packageable nucleic acid comprising a FIV packaging site and a FIV 5' LTR, wherein:

the U3 region of the 5' LTR or a portion thereof is replaced by an expression control sequence which functions in human cells; and the packageable nucleic acid is not capable of self packaging.

2. The packageable nucleic acid of claim 1, comprising a heterologous nucleic acid operably linked to an expression control sequence which functions in human cells.

3. The packageable nucleic acid of claim 1, wherein the packageable nucleic acid includes the R region and U5 region of the 5' LTR.

4. The packageable nucleic acid of claim 1, wherein the packageable nucleic acid comprises a FIV 3' LTR and the U3 region of the 3' LTR or a portion thereof is deleted.

5. A viral particle which comprises the packageable nucleic acid of claim 1.

6. A cell which comprises the packageable nucleic acid of claim 1.

7. The packageable nucleic acid of claim 2, wherein the heterologous nucleic acid encodes a protein.

8. The packageable nucleic acid of claim 2, wherein the heterologous nucleic acid encodes a viral inhibitor.

9. The packageable nucleic acid of claim 2, wherein the heterologous nucleic acid encodes an HIV component.

10. The packageable nucleic acid of claim 2, wherein the expression control sequence is selected from the group consisting of CMV control expression sequence, HIV control expression sequence, HIV LTR control expression sequence, SV40 control expression sequence, pol II control expression sequence, and pol III control expression sequence.

11. The method of claim 8, wherein the viral inhibitor is selected from the group consisting of antisense nucleic acid, ribozyme, decoy nucleic acid, and transdominant nucleic acid.

12. The packageable nucleic acid of claim 10, wherein the expression control sequence is a CMV promoter sequence.

13. The viral particle of claim 5, comprising a viral env polypeptide selected from group consisting of FIV envelope polypeptide, HIV envelope polypeptide, VSV envelope polypeptide, MoMLV envelope polypeptide, and GALV envelope polypeptide.

14. The viral particle of claim 5, comprising a VSV envelope polypeptide.

15. The cell of claim 6 which is human.

16. The cell of claim 6 comprising a packaging nucleic acid plasmid, wherein:
the packaging nucleic acid plasmid comprises a packaging nucleotide sequence which encodes one or more polypeptides necessary for packaging the packageable nucleic acid;
the packaging nucleotide sequence is operably linked to an expression control sequence which functions in human cells; and
the packaging nucleic acid plasmid lacks a functional lentiviral packaging site.

17. The cell of claim 16, wherein the packaging nucleotide sequence encodes a polypeptide selected from the group consisting of viral envelope polypeptide, viral coat polypeptide, cell receptor ligand, antibody, and antibody fragment.

18. The cell of claim 16, wherein the packaging nucleotide sequence encodes one or more viral polypeptides selected from the group consisting of env, gag, and pol.

19. The cell of claim 16, wherein the expression control sequence is selected from the group consisting of CMV control expression sequence, HIV control expression sequence, HIV LTR control expression sequence, SV-40 control expression sequence, pol II control expression sequence, and pol III control expression sequence.

20. The cell of claim 17, wherein the viral env polypeptide is selected from group consisting of FIV envelope polypeptide, HIV envelope polypeptide, VSV envelope polypeptide, MoMLV envelope polypeptide, and GALV envelope polypeptide.

21. The cell of claim 20, wherein the packaging nucleotide sequence encodes a VSV envelope polypeptide.

22. The cell of claim 19, wherein the expression control sequence is a CMV promoter sequence.

23. A method for transfecting a cell with a packageable nucleic acid or transducing a cell with a viral particle comprising a packageable nucleic acid, which comprises contacting the cell with the packageable nucleic acid or the viral particle, wherein:
the packageable nucleic acid comprises a FIV packaging site, a FIV 5' LTR, and a heterologous target nucleic acid operably linked to an expression control sequence;
the U3 region of the 5' LTR or a portion thereof is replaced by the expression control sequence; and
the packagable nucleic acid is not capable of self packaging.

24. The method of claim 23, wherein the expression control sequence functions in human cells.

25. The method of claim 23, wherein the expression control sequence is selected from the group consisting of CMV control expression sequence, HIV control expression sequence, HIV LTR control expression sequence, SV-40 control expression sequence, pol II control expression sequence, and pol III control expression sequence.

26. The method of claim 23, wherein the heterologous nucleic acid encodes a protein.

27. The method of claim 23, wherein the heterologous nucleic acid encodes a viral inhibitor.

28. The method of claim 23, wherein the heterologous nucleic acid encodes an HIV component.

29. The method of claim 23, wherein the cell is a human cell.

30. The method of claim 23, wherein the cell is contacted in vitro.

31. The method of claim 23, wherein the cell is contacted in vivo.

32. The method of claim 23, wherein the packageable nucleic acid includes the R region and U5 region of the 5' LTR.

33. The method of claim 23, wherein the packageable nucleic acid comprises a FIV 3' LTR and the U3 region of the 3' LTR or a portion thereof is deleted.

34. The method of claim 23 which comprises contacting the cell with a packaging nucleic acid plasmid, wherein:
the packaging nucleic acid plasmid comprises a packaging nucleotide sequence which encodes one or more polypeptides necessary for packaging the packageable nucleic acid;
the packaging nucleotide sequence is operably linked to an expression control sequence which functions in human cells; and
the packaging nucleic acid plasmid lacks a functional lentiviral packaging site.

35. The method of claim 23, wherein the viral particle comprises a viral env polypeptide selected from group consisting of FIV envelope polypeptide, HIV envelope polypeptide, VSV envelope polypeptide, MoMLV envelope polypeptide, and GALV envelope polypeptide.

36. The method of claim 23, wherein the cell is a non-dividing human cell.

37. The method of claim 25, wherein the expression control sequence is a CMV promoter sequence.

38. The method of claim 27, wherein the viral inhibitor is selected from the group consisting of antisense nucleic acid, ribozyme, decoy nucleic acid, and transdominant nucleic acid.

39. The method of claim 36, wherein the non-dividing human cell is selected from the group consisting of hemopoietic stem cell, terminally differentiated neuronal cell, and terminally differentiated hematopoietic cell.

40. The method of claim 36, wherein the non-dividing human cell is from a tissue selected from the group consisting of nervous system, eye, hematopoietic system, integument, endocrine system, hepatobiliary system, gastrointestinal tract, genitourinary tract, bone, muscle, cardiovascular system, and respiratory system.

41. The method of claim 30, comprising infusing the transfected cell into a patient.

42. The method of claim 34, wherein the packaging nucleotide sequence encodes a polypeptide selected from the group consisting of viral envelope polypeptide, viral coat polypeptide, cell receptor ligand, antibody, and antibody fragment.

43. The method of claim 34, wherein the packaging nucleotide sequence encodes one or more viral polypeptides selected from the group consisting of env, gag, and pol.

44. The method of claim 34, wherein the viral env polypeptides are selected from group consisting of FIV envelope polypeptide, HIV envelope polypeptide, VSV envelope polypeptide, MoMLV envelope polypeptide, and GALV envelope polypeptide.

45. The method of claim 44, wherein the packaging nucleotide sequence encodes a VSV envelope polypeptide.

46. The method of claim 35, wherein the viral particle comprises a VSV envelope polypeptide.

* * * * *